US011603506B2

(12) United States Patent
Singer et al.

(10) Patent No.: US 11,603,506 B2
(45) Date of Patent: Mar. 14, 2023

(54) PRODUCT COMPRISING A PLASTIC CONTAINER AND A SUBSTANCE COMPOSITION

(71) Applicant: SYMRISE AG, Holzminden (DE)

(72) Inventors: Emilie Singer, Holzminden (DE); Jörn Wiedemann, Holzminden (DE); Sven Siegel, Höxter (DE); Nicole Schulze, Freden (DE)

(73) Assignee: SYMRISE AG, Holzminden (DE)

( * ) Notice: Subject to any disclaimer, the term of this patent is extended or adjusted under 35 U.S.C. 154(b) by 869 days.

(21) Appl. No.: 16/329,437

(22) PCT Filed: Sep. 1, 2016

(86) PCT No.: PCT/EP2016/070625

§ 371 (c)(1),
(2) Date: Feb. 28, 2019

(87) PCT Pub. No.: WO2018/041354

PCT Pub. Date: Mar. 8, 2018

(65) Prior Publication Data

US 2019/0225396 A1 Jul. 25, 2019

(51) Int. Cl.

| | |
|---|---|
| ***A61K 8/18*** | (2006.01) |
| ***A61Q 13/00*** | (2006.01) |
| ***C11B 9/00*** | (2006.01) |
| ***C11D 3/50*** | (2006.01) |
| ***C11D 17/04*** | (2006.01) |

(52) U.S. Cl.

CPC .............. *C11B 9/0069* (2013.01); *C11B 9/00* (2013.01); *C11B 9/003* (2013.01); *C11B 9/0007* (2013.01); *C11B 9/008* (2013.01); *C11B 9/0015* (2013.01); *C11B 9/0019* (2013.01); *C11B 9/0034* (2013.01); *C11B 9/0038* (2013.01); *C11B 9/0046* (2013.01); *C11B 9/0049* (2013.01); *C11B 9/0053* (2013.01); *C11B 9/0061* (2013.01); *C11B 9/0073* (2013.01); *C11B 9/0076* (2013.01); *C11B 9/0084* (2013.01); *C11B 9/0092* (2013.01); *C11D 3/50* (2013.01); *C11D 17/041* (2013.01)

(58) Field of Classification Search

CPC ....... C11D 3/50; C11D 17/041; C11B 9/0046; C11B 9/0053; C11B 9/0092; C11B 9/0073; C11B 9/0034; C11B 9/008; C11B 9/0076; C11B 9/0019; C11B 9/0069; C11B 9/0007; C11B 9/003; C11B 9/0038; C11B 9/0049; C11B 9/0015; C11B 9/0084; C11B 9/0061; C11B 9/00

USPC .................................................. 512/20, 8, 1

See application file for complete search history.

(56) References Cited

U.S. PATENT DOCUMENTS

| | | | |
|---|---|---|---|
| 2003/0036489 A1 | 2/2003 | Liu et al. | |
| 2009/0005280 A1 | 1/2009 | Woo et al. | |
| 2012/0308486 A1 | 12/2012 | Singer et al. | |

FOREIGN PATENT DOCUMENTS

| | | | | |
|---|---|---|---|---|
| JP | H07166190 A | 6/1995 | | |
| JP | 2000053149 A | 2/2000 | | |
| JP | 2000178581 A | 6/2000 | | |
| JP | 2001002618 A | 1/2001 | | |
| JP | 2005029755 A | 2/2005 | | |
| JP | 2007238573 A | 9/2007 | | |
| JP | 2008019441 A | 1/2008 | | |
| JP | 2009155513 A | 7/2009 | | |
| JP | 2010530918 A | 9/2010 | | |
| JP | 2011246200 A | 12/2011 | | |
| JP | 2012111868 A | 6/2012 | | |
| JP | 2015123351 A | 7/2015 | | |
| WO | 2000055292 A1 | 9/2000 | | |
| WO | WO-0055292 A1 * | 9/2000 | ........... | C11D 17/041 |
| WO | 2009001320 A1 | 12/2008 | | |
| WO | WO-2009001320 A1 * | 12/2008 | ............... | A61L 9/01 |
| WO | 2013158477 A1 | 10/2013 | | |

OTHER PUBLICATIONS

International Search Report and Written Opinion dated Dec. 16, 2016 for corresponding PCT Application No. PCT/EP2016/070625.
Database WPI, Week 201184, Thomson Scientific, London, GB, AN 2011-P88853 XP002764898.
“MAUSER and IBA partner on new IBC packaging concept for the food industry,” Germany, 2014, pp. 1-3 XP002764899.
Chinese Office Action dated Jan. 24, 2022 for corresponding Chinese Application No. 201680088813.8.
Japanese Opposition dated Jan. 14, 2022 for corresponding Japanese Application No. 2021-701080.
“Pet/Mx-Nylon Multilayer Bottle,” No. 186, ISSN 0368-6558.
European Office Action dated Nov. 23, 2022 for corresponding European Application No. 16766867.2.

* cited by examiner

*Primary Examiner* — Jessica Whiteley
(74) *Attorney, Agent, or Firm* — Polsinelli PC

(57) ABSTRACT

The present invention primarily relates to a product comprising or consisting of a plastic container (i) comprising or consisting of PE and/or PP and/or PET, and a specific composition (ii) contained in the container, wherein detrimental interactions between the container (i) and the composition (ii) contained therein are minimised.

20 Claims, No Drawings

PRODUCT COMPRISING A PLASTIC CONTAINER AND A SUBSTANCE COMPOSITION

CROSS-REFERENCE TO RELATED APPLICATIONS

This application is a national stage application (under 35 U.S.C. § 371) of PCT/EP2016/070625, filed Sep. 1, 2016, which is incorporated herein by reference in its entirety.

The present invention primarily relates to a product comprising or consisting of a container comprising or consisting of PE and/or PP and/or PET, and a composition contained in the container and comprising or consisting of one or more compound(s) selected from the group (A) consisting of hydrocarbon terpenes with an oxygen percentage of 0, methyl anthranilate derivates with the formula (I) (as described herein), and phenolic derivatives with the formula (II) (as described herein), and/or one or more compound(s) selected from the group (B) consisting of specific cyclic monoterpenes (as described herein), methoxybenzene derivatives with the formula (IV) (as described herein), 2-hydroxybenzoic acid derivatives with the formula (V) (as described herein), benzoate derivatives with the formula (VI) (as described herein), oxomethylbenzene derivatives with the formula (VII) (as described herein), 3-oxopropylbenzene derivatives with the formula (VIII) (as described herein), cyclohex-3-ene-1-carbaldehyde derivatives with the formula (IX) (as described herein), styrene derivatives with the formula (X) (as described herein), acetals with a molar mass of >225 g/mol and calculated water solubility of <0.6 mg/L, and cyclic ethers with a calculated water solubility of <2.5 mg/L, and one or more compounds selected from the group (C) consisting of terpene derivatives (selected from the group consisting of cyclic diterpene ketones (as described herein), acyclic monoterpene esters (as described herein), cyclic monoterpene esters (as described herein), sesquiterpene esters and alcohols (as described herein), acyclic monoterpene aldehydes (as described herein), and acyclic monoterpene alcohols), acetals with a molar mass of <225 g/mol and calculated water solubility of >0.6 mg/L (as described herein), acids (as described herein), alcohols (as described herein), aldehydes (as described herein), esters (as described herein), ethers and cyclic ethers with a calculated water solubility of >2.5 mg/L (as described herein), heterocyclic compounds (as described herein), ketones (as described herein), lactones (as described herein), and nitriles (as described herein), and (D) water and/or one or more solvent(s) (as described herein) and, optionally, (E) one or more surface active compound(s), wherein the total amount of compound(s) of group (A), if present, is 0.5 wt. % or less and the total amount of compound(s) of group (B), if present, is less than 10 wt. %, and wherein the total amount of compound(s) of group (C) is 20 wt. % or less, preferably 10 wt. % or less, in each case based on the total amount of the composition. The present invention also relates to methods of producing said product.

Further aspects of the present invention will arise from the description below, in particular from the examples, as well as from the attached patent claims.

It is a well-known problem that certain substances, in particular fragrance and/or flavouring substances and perfume oils contained in fragrance and/or flavouring compositions interact with the plastic packaging they are contained in for transport, handling and/or storage. Depending on the type of substances and their concentration, they diffuse into or through the plastic and disadvantageously may cause problems such as

- loss of fragrance and/or flavouring substances of the composition,
- deformation of the plastic or packaging, respectively,
- alteration of the properties of the plastic such as rendering it sticky, greasy or porous,
- colour changes of the plastic (e.g. to yellow, brown, glassy/translucent etc.),
- smudging or detaching of prints/labels on the plastic packaging,
- stress fracture corrosion (especially for polyethylene terephthalate-based packaging), and
- destruction of the plastic under the exposure of UV irradiation (partly accelerated through irradiation with specific wavelengths).

It was further found that the damage to the plastic containers described above may be worsened by or occur more often in the presence of surface-active compounds such as tensides, solubilisers and emulsifying agents. This leads to the loss of valuable fragrance and/or flavouring substances from fragrance and/or flavouring substance compositions leading to an altered olfactory impression of the product over time. Moreover, labels on the plastic packaging may become illegible, which is particularly disadvantageous in the case of warning labels. Lastly, products comprising discoloured or deformed packaging are difficult to sell to customers leading to loss of value of the products and to customer complaints.

Plastic containers as mentioned above may, for example, be made from polyethylene (PE), polypropylene (PP) and polyethylene terephthalate (PET) or mixtures thereof. In particular with respect to these materials, there is an ongoing need for products comprising or consisting of plastics used for packaging purposes such as polyethylene (PE), polypropylene (PP) and polyethylene terephthalate (PET) and, in particular, fragrance and/or flavouring substances contained therein, whereby the composition of the fragrance and/or flavouring substances or comprising the same is such that the plastic packaging is neither altered nor damaged during the whole life cycle of the product. Preferably, the composition is such that one or more of the above described detrimental effects, preferably all of these effects, are avoided or at least reduced.

One prior art approach to solve the problem described above has been the use of combination systems of different types of plastics as containers such as, for example, intermediate bulk containers (IBC) made of PE/ethylene vinyl alcohol (EVOH). EVOH, however, despite its advantageous properties, is difficult to synthesise and thus containers comprising this type of plastic are more expensive to produce.

Therefore, the object of the present invention was to provide compositions that are compatible for storage in low cost standard plastic containers such as the ones made from PE and/or PP and/or PET.

Further objects underlying the present invention follow from the description below and the present patent claims.

According to a first aspect of the present invention, the stated object is achieved by a product comprising or consisting of (i) a container comprising or consisting of PE and/or PP and/or PET, preferably being made from LDPE and/or HDPE and/or PP and/or PET, and (ii) a composition contained in the container and comprising or consisting of (A) one or more compound(s) selected from the group (A) consisting of hydrocarbon terpenes with an oxygen percentage of 0, with respect to the molar mass of the compound, preferably cedrene ((1S,2R,5S)-2,6,6,8-tetramethyltricyclo[5.3.1.01.5]undec-8-ene), caryophyllene, ginger oil chinese, gurjun balsam oil, gurjun balsam siam, limonene (4-isopropenyl-1-methyl-cyclohexene), terpinene, phellandrene, pepper black oil, pine needle oil chinese, grapefruit oil, tangerine cravo oil brazil, mandarin oil ital., orange oil brazil, lime oil terpenes, lemon oil terpenes, elemi oil, cymene para, citrylal, pinene alpha, carene delta-3, camphene, pinene beta, dipentene, turpentine oil portug., myrcene, methyl anthranilate derivates with the formula (I)

(I)

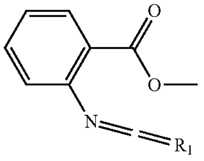

with R1=H, methyl, benzylidene, (2,4-dimethylcyclohex-3-en-1-yl)methylene, 3-(4-tert-butylphenyl)-2-methyl-propylidene, 2,4-dimethylcyclohex-3-en-1-ylidene, [3-(1,3-benzodioxol-5-yl)-2-methyl-propylidene] or (7-hydroxy-3,7-dimethyl-octylidene), and with "N══R1" = "N═R1" or "NH—R1" (i.e. with "══" meaning a single or double bond), preferably methyl anthranilate, dimethylanthranilate, vertosine (methyl 2-[(E)-(2,4-dimethylcyclohex-3-en-1-yl)methyleneamino]benzoate), verdantiol (methyl 2-[(E)-[3-(4-tert-butylphenyl)-2-methyl-propylidene]amino]benzoate), aurantiol (methyl 2-[(E)-(7-hydroxy-3,7-dimethyl-octylidene) amino]benzoate), amandolene (methyl N-benzylideneanthranilate), meaverte (methyl 2-[(2,4-dimethylcyclohex-3-en-1-ylidene)methylamino] benzoate), heliosine (methyl 2-[(E)-[3-(1,3-benzodioxol-5-yl)-2-methyl-propylidene]amino] benzoate), and phenolic derivatives with the formula (II)

(II)

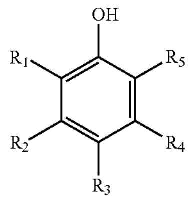

with R1=H, methoxy, ethoxy, or tert-butyl, R2/R4=H, R3=methyl, formyl, allyl, prop-1-enyl, hydroxy, or 3-oxobutyl, R5=H, or tert-butyl, preferably ethyl vanillin, eugenol, vanillin, isoeugenol, BHT ionol, 4-(4-hydroxyphenyl)butan-2-one (Frambinon®), essential oils selected from the group consisting of clove leaves oil, cinnamon leaf oil, and cinnamon leaf oil discolored, and/or (B) one or more compound(s) selected from the group (B) consisting of cyclic monoterpenes, selected from the group consisting of bicyclic epoxy monoterpenes, monocyclic and bicyclic monoterpene alcohols and monoterpene ketones, and having formula (III): $C_{10}H_xO$ (III), with X=14-18, and having a molar mass of 150-154 g/mol, preferably fenchol, isoborneol, borneol, eucalyptol, 1,4-cineol, *eucalyptus* oil, camphor, menthone, isomenthone, carvone, spearmint oil 65% americ. native, methoxybenzene derivatives with the formula (IV)

(IV)

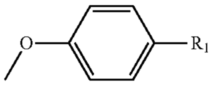

with R1=methyl, prop-1-enyl, allyl, 3-oxobutyl, acetoxymethyl, 2-methyl-3-oxo-butyl, or 3-(2-ethylhexoxy)-3-oxo-prop-1-enyl, preferably cresyl methyl ether para, estragole, 4-(4-methoxyphenyl)butan-2-one (Frambinon® methyl ether), anisyl acetate, canthoxal (3-(4-methoxyphenyl)-2-methyl-propanal), 2-ethyl hexyl (E)-3-(4-methoxyphenyl)prop-2-enoate (Neo Heliopan® AV), 2-hydroxybenzoic acid derivatives with the formula (V)

(V)

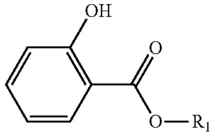

with R1=methyl, ethyl, amyl, isoamyl, hexyl, 2-ethyl hexyl, cyclohexyl, hex-3-enyl, 2-phenyl ethyl, or benzyl, preferably methyl salicylate, ethyl salicylate, amyl salicylate, isoamyl salicylate, hexyl salicylate, 2-ethyl hexyl salicylate, 3-hexenyl salicylate, benzoate derivatives with the formula (VI)

(VI)

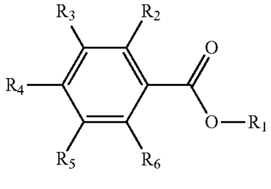

with R1=methyl, ethyl, benzyl, or hexyl, R2=H, hydroxy, or ethoxycarbonyl, R3=H, or methyl, R4=H, or hydroxy, R5=H, R6=H, or methyl, preferably methyl benzoate, evernyl (methyl 2,4-dihydroxy-3,6-dimethyl-benzoate), benzyl benzoate, hexyl benzoate, diethylphtalate, oxomethylbenzene derivatives with the formula (VII)

(VII)

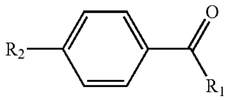

with R1=H, methyl, or phenyl, R2=H, methyl, isopropyl, or methoxy, preferably benzaldehyde, tolylaldehyde para, cuminic aldehyde, acetophenone, methyl acetophenone, benzophenone, anisic aldehyde, 3-oxopropylbenzene derivatives with the formula (VIII)

(VIII)

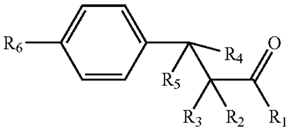

with R1=H, or methyl, R2=H, or methyl, R3=H, or methyl, R4=H, or methyl, R5=H, or methyl, R6=H, ethyl, or isopropyl, preferably florazon (mixture of 3-(4-ethylphenyl)-2,2-dimethyl-propanal and 3-(2-ethylphenyl)-2,2-dimethyl-propanal), floralozone (mixture of 3-(4-ethylphenyl)-2,2-dimethyl-propanal and 3-(2-ethylphenyl)-2,2-dimethyl-propanal), 4-methyl-4-phenyl-pentan-2-one (Vetikon®) and benzylacetone, cyclamen aldehyde (3-(4-isopropylphenyl)-2-methyl-propanal), florhydral (3-(3-isopropylphenyl)butanal), cyclohex-3-ene-1-carbaldehyde derivatives with the formula (IX)

(IX)

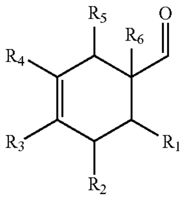

with R1=H, or methyl, R2=H, R3=methyl, 4-hydroxy-4-methyl-pentyl, or 4-methylpent-3-enyl, R4=H, R5=H, R6=H, or methyl, preferably ligustral (mixture of (1R,2S)-2,4-dimethylcyclohex-3-ene-1-carbaldehyde and (1S,2S)-2,4-dimethylcyclohex-3-ene-1-carbaldehyde), vertocitral (mixture of (1R,2S)-2,4-dimethylcyclohex-3-ene-1-carbaldehyde and (1S,2S)-2,4-dimethylcyclohex-3-ene-1-carbaldehyde), lyral (mixture of 4-(4-hydroxy-4-methyl-pentyl)cyclohex-3-ene-1-carbaldehyde and 3-(4-hydroxy-4-methyl-pentyl)cyclohex-3-ene-1-carbaldehyde), vertomugal (mixture of 4-(4-methylpent-3-enyl)cyclohex-3-ene-1-carbaldehyde and 3-(4-methylpent-3-enyl)cyclohex-3-ene-1-carbaldehyde), vernaldehyde (mixture of 3-isohexyl-1-methyl-cyclohex-3-ene-1-carbaldehyde and 4-isohexyl-1-methyl-cyclohex-3-ene-1-carbaldehyde), precyclemone B (mixture of 1-methyl-3-(4-methylpent-3-enyl)cyclohex-3-ene-1-carbaldehyde and 1-methyl-4-(4-methylpent-3-enyl)cyclohex-3-ene-1-carbaldehyde), styrene derivatives with the formula (X)

(X)

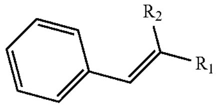

with R1=H, methyl, or hydroxymethyl, R2=H, formyl, methoxycarbonyl, or benzyloxycarbonyl, preferably styrene, methyl cinnamic aldehyde, methyl cinnamate, benzyl cinnamate, cinnamic alcohol, acetals with a molar mass of >225 g/mol and calculated water solubility of <0.6 mg/L, preferably palisandal (1,1-dimethoxycyclododecane), karanal (2-(2,4-dimethylcyclohex-3-en-1-yl)-5-methyl-5-sec-butyl-1,3-dioxane), ethoxymethoxycyclododecane (Amberwood® F), 2',2',8',8'-tetramethylspiro[1,3-dioxolane-2,10'-octahydro-1H-2,4a-methanonapthalene](Ysamber® K), (4aR,5R,7aS,9R)-Octahydro-2,2,5,8,8,9a-hexamethyl-4H-4a,9-methanozuleno[5,6-d]-1,3-dioxole (Ambrocenide®), ketamber (dodecahydro-3,8,8,11a-tetramethyl-5H-3,5a-epoxynaphth[2,1-c]oxepin) (wherein these compounds fulfil the water solubility requirement of <0.6 mg/L), and cyclic ethers with a calculated water solubility of <2.5 mg/L, preferably cedramber (cedryl methyl ether), palisandin (methoxycyclododecane), andrane (alpha cedrene epoxide), ambroxide ((3aS,5aR,9aR)-3a,6,6,9a-tetramethyl-2,4,5,5a,7,8,9,9b-octahydro-1H-benzo[e]benzofuran), ambrox DL (mixture of (3aS,5aR,9aR)-3a,6,6,9a-tetramethyl-2,4,5,5a,7,8,9,9b-octahydro-1H-benzo[e]benzofuran, (3aR,5aS,9aS,9bS)-3a,6,6,9a-tetramethyl-2,4,5,5a,7,8,9,9b-octahydro-1H-benzo[e]benzofuran, (3aS,5aR,9aS,9bR)-3a,6,6,9a-tetramethyl-2,4,5,5a,7,8,9,9b-octahydro-1H-benzo[e]benzofuran, (3aS,5aR,9aS)-3a,6,6,9a-tetramethyl-2,4,5,5a,7,8,9,9b-octahydro-1H-benzo[e]benzofuran, (3aS,5aS,9aS,9bR)-3a,6,6,9a-tetramethyl-2,4,5,5a,7,8,9,9b-octahydro-1H-benzo[e]benzofuran and (3aR,5aR,9aS,9bR)-3a,6,6,9a-tetramethyl-2,4,5,5a,7,8,9,9b-octahydro-1H-benzo[e]benzofuran), galaxolide (4,6,6,7,8,8-hexamethyl-1,3,4,7-tetrahydrocyclopenta[g]isochromene) (wherein these compounds fulfil the water solubility requirement of <2.5 mg/L), and (C) one or more compounds selected from the group consisting of terpene derivatives selected from the group consisting of cyclic diterpene ketones, preferably selected from the group consisting of methyl ionone alpha, methyl ionone beta, methyl ionone gamma, methyl ionone beta, dihydroionone beta, ionone beta, isoradeine, allylionone, damascenone alpha, damascenone beta, damascenone gamma, damascenone delta, damascone alpha, damascone beta, damascone gamma, damascone delta, acyclic monoterpene esters, preferably selected from the group consisting of citronellyl isobutyrate, geranyl butyrate, bornyl acetate, citronellyl acetate, isobornyl acetate, citronellyl formiate, linalyl acetate, neryl acetate, geranyl acetate, geranyl formiate, isoamyl acetate, ethyl linalyl acetate, dihydro myrcenyl acetate, geranyl tiglate, isoamyl isovalerate, tetrahydro linalyl acetate, citronellyl tiglate, cyclic monoterpene esters, preferably selected from the group consisting of isobornyl propionate, terpinyl acetate, fenchyl acetate, menthyl acetate, menthanyl acetate, sesquiterpene esters and alcohols, preferably selected from the group consisting of cedrol, caryophyllene acetate and cedryl acetate, acyclic monoterpene aldehydes, preferably selected from the group consisting of 2,6,10-trimethylundec-9-enal (Farenal®), (5E)-2,6,10-trimethylundeca-5,9-dienal (Profarenal®), hydroxyl citronellal, citronellal, citral, *eucalyptus* oil *citriodora*, lemongrass oil cochin, and acyclic monoterpene alcohols, preferably selected from the group consisting of dihydromyrcenol, linalool, terpineol, citronellol, geraniol, nerol, nerolidol, farnesol, hydroxyl citronellol, isoamyl alcohol, osyrol (7-methoxy-3,7-dimethyl-octan-2-ol), tetrahydro geraniol, tetrahydro linalool, tetrahydro muguol (mixture of tetrahydro myrcenol and tetrahydro linalool), tetrahydro myrcenol, ethyl linalool, isobornyl cyclohexanol, 1-[(1S,6S)-2,2,6-trimethylcyclohexyl]pentan-3-ol (Madranol®), 1-(2,2,6-trimethylcyclohexyl)hexan-3-ol (Timberol®), thymol, mayol ((4-isopropylcyclohexyl)methanol), dihydro terpineol, menthol, menthol rac., pine oil, coriander oil, palmarosa oil, acetals with a molar mass of <225 g/mol and calculated water solubility of >0.6 mg/L, preferably selected from the group consisting of 2-isobutyl-4-vinyl-1,3-dioxolane, 6,6-dimethoxy-2,5,5-trimethyl-hex-2-ene (Amarocit®), hyacinth body, floropal, magnolan, (2R,4S)-2-methyl-4-phenyl-1,3-dioxolane (Jacinthaflor®), phenylacetaldehyde dimethyl acetal, 4,4a,5,9b-tetrahydroindeno[1,2-d][1,3]dioxine (Indoflor®), citral diethyl acetal, hydroxyl citronellal dimetacetal, phenylacetaldehyde glyceryl acet ((2-benzyl-1,3-dioxolan-4-yl) methanol), heliotropin (1,3-benzodioxole-5-carbaldehyde), helional (3-(1,3-benzodioxol-5-yl)-2-methyl-propanal), particularly preferably 2-isobutyl-4-vinyl-1,3-dioxolane (wherein these compounds fulfil the water solubility requirement of >0.6 mg/L), acids, preferably selected from the group consisting of acetic acid, benzoic acid, butyric acid, pelargonic acid, phenylacetic acid, alcohols, preferably selected from the group consisting of phenylethyl alcohol, ambrinol ((2S,4aS)-2,5,5-trimethyl-1,3,4,4a,6,7-hexahydronaphthalen-2-ol), amber core (mixture of 1-[(1R,2R)-2-tert-butylcyclohexoxy]butan-2-ol, 1-[(1S,2R)-2-tert-butylcyclohexoxy]butan-2-ol and 2-(2-tert-butylcyclohexoxy)butan-1-ol), 2-methyl-4-(2,2,3-trimethylcyclopent-3-en-1-yl)butan-1-ol (Brahmanol®), kohinool, mugetanol (mixture of cis-1-(4-isopropylcyclohexyl)ethanol and trans-1-(4-isopropylcyclohexyl)ethanol), polysantol ((E)-3,3-dimethyl-5-(2,2,3-trimethylcyclopent-3-en-1-yl)pent-4-en-2-ol), undecavertol, alcohol C12, jasmol, sandalore (mixture of 3-methyl-5-(2,2,3-trimethylcyclopent-3-en-1-yl)pentan-2-ol and 6-(2,2,3-trimethylcyclopent-3-en-1-yl)hexan-3-ol), anisyl alcohol, hexanol, octanol, decanol, benzyl alcohol, butyl cyclohexanol para-tert., decenol-9, dimethyl benzyl carbinol, ebanol (mixture of (E,2S,3R)-3-methyl-5-(2,2,3-trimethylcyclopent-3-en-1-yl)pent-4-en-2-ol and (E,2R,3R)-3-methyl-5-(2,2,3-trimethylcyclopent-3-en-1-yl) pent-4-en-2-ol), florosa, freesiol (corps 119, 2,6-dimethylheptan-2-ol), furaneol, cis-3-hexenol, isononanol, 2,2-dimethyl-3-(m-tolyl)propan-1-ol (Majantol®), methyl methoxy butanol-3,3, muguetalcohol (2,2-dimethyl-3-phenyl-propan-1-ol), phenoxanol (3-methyl-5-phenyl-pentan-1-ol), phenoxyethyl alcohol, phenyl dimethyl carbinol, phenylethyl methylethyl carbinol, phenylpropyl alcohol, (2-methyl-5-phenyl-pentan-1-ol) (Rosaphen®), sandal mysore core ((E)-2-methyl-4-(2,2,3-trimethylcyclopent-3-en-1-yl)but-2-en-1-ol), (E)-2-ethyl-4-(2,2,3-trimethylcyclopent-3-en-1-yl)but-2-en-1-ol (San-Dranol®), styralyl alcohol, 4-isopentylcyclohexanol (Symrose®), dihydro eugenol, propenyl guaethol, cresol para, ambrinolepoxide ((1aR,4aS,7S,8aS)-4,4,7-trimethyl-2,3,4a,5,6,8-hexahydro-1aH-naphtho[1,8a-b]oxiren-7-ol), aldehydes, preferably selected from the group consisting of aldehyde C12 MNA, neocyclo citral, aldehyde C11 MOA, hexyl cinnamic aldehyde alpha, cyclomyral, amyl cinnamic aldehyde, decanal, 2,6-dimethylhept-5-enal (Melonal®), nonanal, isononyl aldehyde S, octanal, aldehyde C11 iso, intreleven aldehyde (mixture of undec-10-enal, 9-undecenal and 8-undecenal), lilial (3-(4-tert-butylphenyl)-2-methyl-propanal), hexanal, heptanal, silvial (3-(4-isobutylphenyl)-2-methyl-propanal), 2-trans-hexenal, bourgeonal (3-(4-tert-butylphenyl)propanal), scentenal (octahydro-5-methoxy-4,7-methano-1H-indene-2-carboxaldehyde), phenylacetaldehyde, mandarin aldehyde (2E-dodecenal), esters, preferably selected from the group consisting of pyroprunat ((2-cyclopentylcyclopentyl) (E)-but-2-enoate), hercolyn D-E (mixture of methyl 7-isopropyl-1,4a-dimethyl-2,3,4,5,6,7,8,9,10,10a-decahydrophenanthrene-1-carboxylate and methyl 7-isopropyl-1,4a-dimethyl-2,3,4,9,10,10a-hexahydrophenanthrene-1-carboxylate), fruitate, cyclabute (3a,4,5,6,7,7a-hexahydro-4,7-methano-1H-inden-5-yl 2-methyl propanoate), poivrol (mixture of methyl (1S,4R,5R)-4-isopropyl-1-methyl-bicyclo[2.2.2]oct-2-ene-5-carboxylate, methyl (1S,4R,5S)-4-isopropyl-1-methyl-bicyclo [2.2.2]oct-2-ene-5-carboxylate, methyl (1R,2S,4R)-4-isopropyl-1-methyl-bicyclo[2.2.2]oct-5-ene-2-carboxylate and methyl (1R,2R,4R)-4-isopropyl-1-methyl-bicyclo[2.2.2]oct-5-ene-2-carboxylate), guaiyl acetate, herbyl propionate (hexahydro-4,7-methanoinden-5(or 6)-yl propionate), vetiveryl acetate, nopyl acetate, hydroherbaflorat, herbaflorat (hexahydro-4,7-methanoinden-(5 and 6)-yl acetate), ethyl cinnamate, phenylethyl cinnamate, isoeugenyl methyl ether, isoeugenyl acetate, eugenyl acetate, ethyl benzoate, isobutyl salicylate, prenyl salicylate, dimethyl benzyl carbonyl butyrate, phenylethyl isovalerate, benzyl butyrate, benzyl isobutyrate, dimethyl benzyl carbonyl acetate, phenylethyl isobutyrate, benzyl propionate, phenylethyl acetate, (1,3-dimethyl-3-phenyl-butyl) acetate (Vetikolaceate®), benzyl acetate, ethyl phenyl acetate, methyl phenyl acetate, styralyl acetate, phenylethyl phenylacetate, benzyl formiate, 2-phenoxyethyl 2-methylpropanoate (Phenirate®), benzyl phenylacetate, aldehyde C16 so-called, allyl phenoxy acetate, cresyl phenyl acetate para, rosacetate, isopropylmyristate, hexyl caproate, ethyl caprinate, decyl acetate, ethyl caprylate, hexyl butyrate, hexyl isobutyrate, ethyl heptoate, isoamyl butyrate, butyl butyrate, allyl heptoate, ethyl caproate, manzanate, neononyl acetate, ethyl methyl butyrate-2, frutinat, isopentyrate, allyl caproate, ethyl butyrate, ethyl isovalerate, amyl acetate, hexyl acetate, ethyl isobutyrate, butyl acetate, isobutyl acetate, ethyl propionate, cis-3-hexenylacetate, [(Z)-hex-3-enyl]methyl carbonate (Leafovert®), prenyl acetate, methyl octin carbonate, allyl amyl glycolate, ethyl acetate, butyl butyryl lactate, diethyl malonate, ethyl acetoacetate, (3-hydroxy-2,2,4-trimethyl-pentyl) 2-methylpropanoate (Symfresh® NX), allyl cyclohexyl propionate, givescone (mixture of ethyl 2,3,6,6-tetramethylcyclohex-2-ene-1-carboxylate and ethyl 2-ethyl-6,6-dimethyl-cyclohex-2-ene-1-carboxylate), mintonat (mixture of [(1S,5S)-3,3,5-trimethylcyclohexyl]acetate and [(1R,5S)-3,3,5-trimethylcyclohexyl]acetate), oryclon ((4-tert-butylcyclohexyl) acetate), agrumex HC ([(1S,2S)-2-tert-butylcyclohexyl]acetate), aphermate (1-(3,3-dimethylcyclohexyl)ethyl formate), cyclohexyl ethyl acetate, datilat (1-cyclohexylethyl (E)-but-2-enoate), helvetolide (2-[1-(3,3-dimethylcyclohexyl)ethoxy]-2-methyl-propyl]propanoate), myraldyl acetate (mixture of [3-(4-methylpent-3-enyl)cyclohex-3-en-1-yl]methyl acetate and [4-(4-methylpent-3-enyl)cyclohex-3-en-1-yl]methyl acetate), cyclohexyl acetate, allyl 2-(cyclohexoxy) acetate (Cyclogalbanate®), jasmopyrane ((3-pentyltetrahydropyran-4-yl) acetate), jessemal ((3-butyl tetrahydro-5-methyl-2H-pyran-4-yl) acetate, ethylene brassylate (1,4-dioxacycloheptadecane-5,17-dione), ethylene dodecanedioate arova N, ethyl 2-(2,4-dimethyl-1,3-dioxolan-2-yl)acetate (Fragolane®), hedione (mixture of methyl 2-[(1S,2S)-3-oxo-2-pentyl-cyclopentyl]acetate and methyl 2-[(1S,2R)-3-oxo-2-pentyl-cyclopentyl] acetate, jasmaprunat (ethyl 2-(2-methyl-1,3-dioxolan-2-yl)acetate), jasmopol AC1300 (methyl 2-hexyl-3-oxo-cyclopentanecarboxylate), maltol isobutyrate, triethyl citrate, ethers and cyclic ethers with a calculated water solubility of >2.5 mg/L, preferably selected from the group consisting of anther, rose oxide HC (mixture of (2R,4S)-4-methyl-2-(2-methylprop-1-enyl)tetrahydropyran and (2S,4S)-4-methyl-2-(2-methylprop-1-enyl)tetrahydropyran), rose oxide L (mixture of (2R,4S)-4-methyl-2-(2-methylprop-1-enyl)tetrahydropyran and (2S,4S)-4-methyl-2-(2-methylprop-1-enyl)tetrahydropyran), rose oxide inactive (mixture of (2R,4S)-4-methyl-2-(2-methylprop-1-enyl)tetrahydropyran and (2S,4S)-4-methyl-2-(2-methylprop-1-enyl)tetrahydropyran), diphenyl oxide, phenylethyl methyl ether, dibenzyl ether, kephalis (4-(1-ethoxyvinyl)-3,3,5,5-tetramethyl-cyclohexanone), linalool oxide, dowanol DPM (3-(3-methoxypropoxy)propan-1-ol) (wherein these compounds fulfil the water solubility requirement of >2.5 mg/L), heterocyclic compounds, preferably selected from the group consisting of oxanthia (mixture of (2S,4R)-2-methyl-4-propyl-1,3-oxathiane and (2R,4R)-2-methyl-4-propyl-1,3-oxathiane), isobutyl quinolone, isobutyl quinolone DL, sulfurol (2-(4-methylthiazol-5-yl)ethanol), indol, ketones, preferably selected from the group consisting of cyclohexadecanone (Isomuscone®), vertofix, veloutone, muscenone, 4-[(3,3-dimethylnorbornan-2-yl)methyl]-2-methyl-cyclohexanone (Aldron®), isolongifolanon (octahydrotetramethyl methanoazulenone), (8E)-cyclohexadec-8-en-1-one (Globanone®), 2,4,4,7-tetramethyloct-6-en-3-one (Claritone®), iso e super (mixture of 1-[(2R,3R)-2,3,8,8-tetramethyl-1,3,4,5,6,7-hexahydronaphthalen-2-yl]ethanone, 1-(2,3,8,8-tetramethyl-1,3,5,6,7,8a-hexahydronaphthalen-2-yl)ethanone and 1-[(2S,3S)-2,3,8,8-tetramethyl-1,3,5,6,7,8a-hexahydronaphthalen-2-yl]ethanone), (8E)-cyclohexadec-8-en-1-one (Aurelione®), projasmone P (2-heptylcyclopentanone), frescomenthe (2-sec-butylcyclohexanone), dynascone (mixture of 1-(5,5-dimethylcyclohexen-1-yl)pent-4-en-1-one, 1-(3,3-dimethylcyclohexen-1-yl) pent-4-en-1-one and (E)-1-(2,6,6-trimethylcyclohex-2-en-1-yl)but-2-en-1-one), galbascone (1-(5,5-dimethylcyclohexen-1-yl)pent-4-en-1-one), undecanone-2, koavone (mixture of (E)-3,4,5,6,6-pentamethylhept-4-en-2-one, 3,5,6,6-tetramethyl-4-methylene-heptan-2-one and (E)-3,4,5,6,6-pentamethylhept-3-en-2-one), tonalide (1-(1,1,2,4,4,7-hexamethyltetralin-6-yl)ethanone), nerolione (1-(3-methylbenzofuran-2-yl)ethanone), octanone-2, cashmeran (1,1,2,3,3-pentamethyl-2,5,6,7-tetrahydroinden-4-one), orivone (4-(1,1-dimethylpropyl)cyclohexanone), azarbre (mixture of 3,5-diethyl-2,5-dimethyl-cyclohex-2-en-1-one and 3,5-diethyl-5,6-dimethyl-cyclohex-2-en-1-one), methyl heptenone-6,5,2, dihydro jasmine (3-methyl-2-pentyl-cyclopent-2-en-1-one), jasmine cis (3-methyl-2-[(Z)-pent-2-enyl]cyclopent-2-en-1-one), acetanisole, calone 1951 (7-methyl-1,5-benzodioxepin-3-one), acetyl methyl carbinol, crysolide (1-(6-tert-butyl-1,1-dimethyl-indan-4-yl)ethanone), ethyl maltol, maltol, methyl cyclopentenolone-3,2,2, lactones, preferably selected from the group consisting of oxacyclohexadecan-2-one (Macrolide® supra), mixture of (12E)-1-oxacyclohexadec-12-en-2-one, (12Z)-1-oxacyclohexadec-12-en-2-one and (13E)-1-oxacyclohexadec-13-en-2-one (Globalide®), ambrettolide ((10E)-1-oxacycloheptadec-10-en-2-one), aldehyde C14 so-called, aldehyde C18 so-called, decalactone, docecalactone, coumarin, heptalactone, octahydro coumarin, octalactone, methyl laitone (8-methyl-4-oxaspiro [4.5]decan-3-one), and nitriles, preferably selected from the group consisting of ozonil, clonal, 2-(2,2,3-trimethylcyclopent-3-en-1-yl)acetonitrile (Cantryl®), lemonile ((2E, 6E)-3,7-dimethylnona-2,6-dienenitrile), agrunitril (3,7-dimethyloct-6-enenitrile), peonile (2-cyclohexylidene-2-phenyl-acetonitrile), cinnamylnitrile, citronitrile ((E)-3-methyl-5-phenyl-pent-2-enenitrile), and (D) water and/or one or more solvent(s) selected from the group consisting of ethanol, dipropylene glycol (DPG), diethylphtalate (DEP), propylene glycol (PG), isopropylmyristate (IPM), isopropylpalmitate (IPP) triethylcitrate (TEC), 2-propanol, triacetin (TRI), 1,2-propanediol, 1,3-propanediol, propanetriol, 1,2-pentanediol (Hydrolite®-5), 1,2-hexanediol (Hydrolite®-6), 1,2-octanediol (Hydrolite®-8), 1,2-decanediol (SymClariol®), dodecanol, 4-hydroxy-acetophenone (SymSave® H), glycerin, butylenes glycol, pentylene glycol, hexylene glycol, decylene glycol, propylene carbonate, butylenes carbonate, glycerin carbonate, 2-benzylheptanol, laurylalcohol, trimethyl-hydroxypentyl-isobutyrat, glycerylcaprylate, ethylhexylglycerin, benzylbenzoate (BB), Isoparaffine, glycol ether, dowanol, preferably selected from the group consisting of ethanol, DPG, PG, IPM, TEC, 1,2-propanediol, 1,3-propanediol, propanetriol, 1,2-pentanediol (Hydrolite®-5), 1,2-hexanediol (Hydrolite®-6), 1,2-octanediol (Hydrolite®-8), 1,2-decanediol (SymClariol®), dodecanol, 4-hydroxy-acetophenone (SymSave® H), glycerine, isopar-L, more preferably selected from the group consisting of ethanol, DPG, IPM, 1,2-propanediol, 1,3-propanediol, and, optionally, (E) one or more surface active compound(s) selected from the group consisting of alkyl carboxylate, alkyl sulfonate, alkyl sulphate, alcohol polyglycol ether sulfate, quaternary ammonium cations, quaternary ammonium ester, alcohol polyglycol ether, N-(Acylaminoalkyl)-betaine, polyethylene glycol alkyl ether, alkyl benzene sulfonate, TEA-esterquat, more preferably selected from the group consisting of lauryl ether sulfate, betaine, lauryl alkyl sulfate, PEG hydrogenated castor oil, laureth-5, laureth-6, laureth-7, Dialkylesterammoniumethosulfate, sodium stearate, sodium palmitate, polyethylene glycol, zinc stearate, sodium caprylate, lauric acid, Isopar-L, sodium dodecyl benzene sulfonate, Di hydrogenated Tallowethyl Hydroxyethylmonium Methosulfate, wherein the total amount of compound(s) of group (A), if present, is 0.5 wt. % or less and the total amount of compound(s) of group (B), if present, is less than 10 wt. %, and wherein the total amount of compound (s) of group (C) is 20 wt. % or less, preferably 10 wt. % or less, in each case based on the total amount of the composition.

In the context of the own studies underlying the present invention, it was surprisingly found that if the compounds contained in composition (ii) are categorized as defined above and if the total amounts of compound(s) of group (A) and of group (B), if present, and of group (C) are restricted to the amounts in the composition as defined above, a particularly stable product may be obtained, wherein composition (ii) as defined above does not interact with the plastic of container (i) as defined above to a significant extent. In other words, one or more of the detrimental effects mentioned above can be avoided or at least reduced.

Furthermore, due to less interactions with the plastic of the container, especially less deformation, it is possible to reduce the wall thickness of the container and to reduce the amount of packaging material.

The water solubility of the compounds is preferably calculated via the molecular structure by the program "Epi-Win" of Howard+Meylan. This calculated value describes the water solubility of a compound in mg/L at room temperature. The higher the value, the more of the compound is soluble in water.

In the context of the present invention a container (i) comprising or consisting of PE and/or PP and/or PET, preferably being made from PE and/or PP and/or PET, is meant to be for example a container that either comprises or consists of a single type of plastic selected from the group consisting of PE, PP and PET, or comprises or consists of layers or blends of two or three types of different plastics selected from the group consisting of PE, PP and PET.

Moreover, the term "polyethylene (PE)", in the context of the present invention, includes all of the different forms of PE classified by their differing density and branching, such as ultra-high-molecular-weight polyethylene (UHMWPE), ultra-low-molecular-weight polyethylene (ULMWPE or PE-WAX), high-molecular-weight polyethylene (HMWPE), high-density polyethylene (HDPE or PEAD), high-density cross-linked polyethylene (HDXLPE), cross-linked polyethylene (PEX or XLPE), medium-density polyethylene (MDPE), linear low-density polyethylene (LLDPE), low-density polyethylene (LDPE), very-low-density polyethylene (VLDPE), chlorinated polyethylene (CPE), etc, preferably HDPE or LDPE.

The term "polypropylene (PP)", in the context of the present invention, also includes all of the different possible types of PP such as isotactic PP, syndiotactic PP, atactic PP, high crystalline PP (HcPP), random copolymers (RACO) of PP, block copolymers (HECO) of PP, uniaxially or biaxially oriented PP (BOPP), etc.

The term "polyethylene terephthalate (PET)", in the context of the present invention, includes the different types of PET, such as polyethylenterephthalate and polyethylenterephthalate glycol.

In the context of the present invention, the product as defined above comprises or consists of (i) a container as defined above, and (ii) a composition contained in the container and comprising or consisting of (A) one or more compound(s) selected from the group (A) as defined above, and/or (B) one or more compound(s) selected from the group (B) as defined above, and (C) one or more compounds selected from the group (C) as defined above, and (D) water and/or one or more solvent(s) as defined above, and, optionally, (E) one or more surface active compound(s) as defined above, wherein the total amount of compound(s) of group (A), if present, is 0.5 wt. % or less and the total amount of compound(s) of group (B), if present, is less than 10 wt. %, and wherein the total amount of compound (s) of group (C) is 20 wt. % or less, preferably 10 wt. % or less, in each case based on the total amount of the composition.

That is, according to the invention, compound(s) of group (A) as defined above and compound(s) of group (B) as defined above may both be present in composition (ii) at the same time or, optionally, only one of either compound(s) of group (A) or compound(s) of group (B) as defined above may be present in composition (ii), whereas compound(s) of group (C) and (D) as defined above both have to be present in composition (ii), and compound(s) of group (E) as defined above may optionally be present.

Moreover, within the scope of the present text, an embodiment is disclosed, wherein the compound(s) of group (C) as defined above may be absent from composition (ii) (i.e. composition (ii) may not comprise one or more compound (s) of group (C) as defined above), preferably in case (a) compound(s) of group (E) as defined above is present in composition (ii).

The compositions (ii) as defined above are preferably used to produce or are preferably perfumed and/or flavoured products. The composition (ii) can be in liquid or in solid form, can e.g. be spray dried or encapsulated. The substance compositions (ii) as defined above may, according to one embodiment, thereby be used in concentrated forms or diluted solutions for the manufacture of perfumed and/or flavoured products.

Preferred products according to the invention disclosed herein or, respectively, preferred compositions (ii) as described above are perfumed items selected from the group consisting of liquid detergents, powder detergent, fabric softeners, shampoos, shower gels, liquid soaps, dishwashs, conditioners, cleaners, body lotions, crémes, water-containing air fresheners, in-wash fabric perfumes or scent boosters, fabric (re)freshener sprays, hygiene or care products, in particular in the range of body and hair care, cosmetic and household, and flavored items, selected from the group consisting of foodstuffs, semi luxury foods, drinks, oral care products (e.g. oral hygiene products) or pharmaceutical products.

Composition (ii) as defined above may also comprise further base materials and further adjuvants and additives (i.e. further to the compound(s) of groups (A) to (E)). The base materials to be used for the formulation of composition (ii) depend on the nature of the product and are known to the skilled person. Further adjuvants and additives are for example:

Preservatives, preferably those described in US 2006/0089413, abrasives, antiacne and sebum reducing agents, preferably those described in WO 2008/046791, compounds against ageing of the skin, preferably those described in WO 2005/123101, antibacterial agents, anti-cellulitis agents, antidandruff agents, preferably those described in WO 2008/046795, antiphlogistic agents, irritation-preventing agents, anti-irritants (anti-inflammatory, irritation-preventing and irritation-inhibiting agents), preferably those described in WO 2007/042472 and US 2006/0089413, antimicrobial agents, preferably those described in WO 200/23101, antioxidants, preferably those described in WO 2005/123101, astringents, antiseptic agents, antistatics, binders, buffers, support materials, preferably those described in WO 2005/123101, chelating agents, preferably those described in WO 2005/123101, cell stimulants, cleansing agents, conditioning agents, depilators, deodorizing agents and antiperspirants, preferably those described in WO 2005/123101, softeners, emulsifiers, preferably those described in WO 2005/123101, enzymes, other ethereal oils, preferably those described in US 2008/0070825, insect repellents, preferably those described WO 2005/123101, fibers, film-formers, other fixers, foaming agents, foam stabilizers, substances to prevent foaming, foam boosters, fungicides, gelling agents, gel forming agents, preferably those described in WO 205/12301, hair care products, hair styling agents, hair straightening agents, moisture regulators (moisture-donating agents, moisturizing substance, moisture-retaining substances), preferably those described in WO 2005/123101, osmolytes, preferably those described in WO 2005/123101, compatible solutes, preferably those described in WO 01/76572 and WO 02/15868, bleaching agents, strengthening agents, stain-removing agents, optically brightening agents, impregnating agents, dirt-repellent agents, friction-reducing agents, lubricants, moisturizing cremes, ointments, opacifying agents, plasticizing agents, covering agents, polish, gloss agents, polymers, preferably those described in WO 2008/046676, powders, proteins and protein hydrolysates, preferably those described in WO 2005/123101 and WO 2008/046676, lipid replenishing cremes, polishing agents, skin soothing agents, skin cleansing agents, skin care agents, skin repair agents, preferably containing cholesterol and/or fatty acids and/or ceramides and/or pseudoceramides, preferably those described in WO 2006/053912, skin lightening agents, preferably those described in WO 2007/110415, skin-protecting agents, skin-softening agents, skin-cooling agents, preferably those described in WO 2005/123101, skin-warming agents, preferably those described in WO 2005/123101, stabilizers, UV-absorbing agents and UV-filters, preferably those described in WO 2005/123101, benzylidene-beta-dicarbonyl compounds, preferably those described in WO 2005/107692, alpha-benzoyl-cinnamic acid nitriles, preferably those described in WO 2006/015954, AhR-receptor antagonists, preferably those described in WO 2007/128723 and WO 2007/060256, detergents, fabric conditioners, suspending agents, skin tanning agents preferably those described in WO 2006/045760, thickening agents, vitamins, preferably those described in WO 2005/123101, oils, waxes and other fats, preferably those described in WO 2005/123101, phospholipids, preferably those described in WO 2005/123101, fatty acids (saturated fatty acids and mono- or polyunsaturated fatty acids and $\alpha$-hydroxy acids and polyhydroxy-fatty acids), preferably those described in WO 2005/123101, condensers, dyestuffs and color-protecting agents and pigments, preferably those described in WO 2005/123101, anti-corrosive agents, alcohols and polyols, preferably those described in WO 2005/123101, other surfactants, preferably those described in WO 2005/123101, animal extracts, yeast extracts, extracts from algae or microalgae, electrolytes, condensers, organic solvents, preferably those described in WO 2005/123101, hair growth modulating agents (hair growth promoting or hair growth inhibiting), preferably those described in EP 2168570 and EP 2193785 or silicones and silicone derivatives preferably those described in WO 2008/046676, oxygen-releasing compounds, preferably sodium carbonate peroxyhydrate, percarbonates, perborates, sodium hypochlorite, potassium hypochlorite, salts, preferably sodium sulfate, calcium phosphate, calcium silicate, magnesium silicate, sodium carbonate, fillers or bulking agents.

Preferably, the further base materials, if present, may be comprised in composition (ii) as defined above in amounts of up to 95 wt. %, preferably in an amount of from 0.0001 wt. % to 90 wt. %, more preferably in an amount of from 0.01 wt. % to 80 wt. %, based on the total weight of the composition. Preferably, the further adjuvants and additives, if present, may be comprised in composition (ii) as defined above in amounts of up to 95 wt. %, preferably in an amount of from 0.0001 wt. % to 80 wt. % based on the total weight of the composition.

In case that compounds fall under the category of compound(s) of group (A) or (B) of composition (ii) as defined above and also, at the same time, fall under the category of compound(s) of group (C) of composition (ii) as defined above, they shall be allocated to the group of compound(s) of group (A) or (B), respectively, and not to compound(s) of group (C) in terms of calculating the proportions of the respective components contained in composition (ii) in wt. % based on the total amount of the composition (ii). The same applies to any other compounds that may be present in the composition (ii) and fall under groups (A) and (B) as defined herein.

In a preferred embodiment according to the present invention, composition (ii) as defined above comprises one or more compounds selected from the group consisting of acetals with a molar mass of <225 g/mol and calculated water solubility of >0.6 mg/L (see group (C)), preferably selected from the group consisting of 2-isobutyl-4-vinyl-1,3-dioxolane, 6,6-dimethoxy-2,5,5-trimethyl-hex-2-ene (Amarocit®), hyacinth body, floropal, magnolan, (2R,4S)-2-methyl-4-phenyl-1,3-dioxolane (Jacinthaflor®), phenylacetaldehyde dimethyl acetal, 4,4a,5,9b-tetrahydroindeno[1,2-d][1,3]dioxine (Indoflor®), citral diethyl acetal, hydroxyl citronellal dimetacetal, phenylacetaldehyde glyceryl acet, heliotropin, helional (wherein these compounds fulfil the water solubility requirement of >0.6 mg/L), particularly preferably 2-isobutyl-4-vinyl-1,3-dioxolane.

In a preferred embodiment according to the present invention, the container (i) of the product defined above comprises or consists of PE and/or PP, preferably PE, more preferably HDPE and/or LDPE, or is made of PE and/or PP, preferably PE, more preferably HDPE and/or LDPE.

Plastic containers used for packaging of different types of products are made from PE and/or PP since they are stable and affordable materials with high chemical stability. They are food-safe, can be cleaned easily and have high UV resistance. Thus, they are the ideal choice for packaging the products as defined above.

In another preferred embodiment according to the present invention, the container (i) of the product defined above is a container for transport, handling and/or storage, preferably in the form of a wrapping, an encasement, a packaging, a shell, a coating, or an envelope, preferably a packaging.

In another preferred embodiment according to the present invention, the container (i) of the product defined above is an imprinted container and/or a container with an imprinted label.

In another preferred embodiment according to the present invention, the container (i) of the product defined above is a patterned or a flat container with a wall thickness of 0.01 mm-1.5 mm, preferably with a wall thickness of 0.05 mm-0.9 mm, more preferably with a wall thickness of 0.1-0.7 mm, especially preferred with a wall thickness of 0.15 mm-0.25 mm.

A person skilled in the art knows and may use all of the common, suitable forms of containers to transport, handle and/or store composition (ii) as defined above.

Another preferred embodiment according to the present invention is a product as defined above, wherein the total amount of compound(s) of group (A), if present, is in the range of from 0.05 wt. % to 0.5 wt. % and the total amount of compound(s) of group (B), if present, is in the range of from 0.01 wt. % to less than 10 wt. %, more preferred in the range of from 0.01 wt. % to 1.25 wt. %, in each case based on the total amount of the composition.

In the context of the underlying study, it was surprisingly found that in a particularly preferred embodiment of the present invention the total amounts of the compound(s) of group (A), if present, and of group (B), if present, in composition (ii) are restricted to the ranges as defined above. Such composition (ii) leads to a particularly stable product, wherein the interaction of composition (ii) as defined above with the plastic of container (i) as defined above is reduced to a minimum and one or more, preferably all of the above described detrimental effects are avoided or reduced.

Another preferred embodiment according to the present invention is a product as defined above, wherein the total amount of water (component (D)), if present, is in the range of from 0.0001 wt. % to 99 wt. %, preferably 0.1 wt. % to 99 wt. %, more preferably 35 wt. % to 99 wt. %, based on the total amount of the composition.

A specific, exemplary embodiment according to the present invention is a detergent powder product as defined above, wherein the total amount of water (component (D)), if present, is in the range of from 0.0001 wt. % to 5 wt. %, based on the total amount of the composition.

Another preferred embodiment according to the present invention is a product as defined above, wherein the total amount of the solvent(s) according to component (D), if present, is in the range of from 0.001 wt. % to 99 wt. %, based on the total amount of the composition.

A preferred embodiment according to the present invention is a detergent powder product as defined above, wherein the total amount of the solvent(s) according to component (D), if present, is in the range of from 0.001 wt. % to 2 wt. %, based on the total amount of the composition.

Another preferred embodiment according to the present invention is a product as defined above, wherein the total amount of the surface active compound(s) according to component (E), if present, is in the range of from 0.5 wt. % to 50 wt. %, based on the total amount of the composition.

As indicated above, the product or a composition (ii) as defined above preferably comprises or is selected from the group consisting of perfume extracts, eaux de parfum, eaux de toilettes, aftershaves, eaux de colognes, preshave products, splash colognes and perfumed freshening wipes, acidic, alkaline and neutral cleaners, such as, for example, floor cleaners, window cleaners, dishwashing detergents, bath and sanitary cleaners, scouring milk, solid and liquid WC cleaners, pulverulent and foam carpet cleaners, liquid laundry detergents, pulverulent laundry detergents, laundry pretreatment agents, such as bleaches, soaking agents and stain removers, fabric softeners, washing soaps, washing tablets, disinfectants, surface disinfectants, in-wash perfume, in-wash scent booster and air fresheners in liquid or gel form or deposited on a solid carrier, aerosol sprays, waxes and polishes, such as furniture polishes, floor waxes, shoe creams, and body care compositions, such as, for example, solid and liquid soaps, shower gels, shampoos, conditioners, shaving soaps, shaving foams, bath oils, deodorants and antiperspirants, such as, for example sprays, roll-ons, creams, sticks, solids, cosmetic emulsions of the oil-in-water, water-in-oil and water-in-oil-in-water type, such as, for example, skin creams and lotions, face creams and lotions, sunscreen creams and lotions, after sun creams and lotions, hand creams and lotions, foot creams and lotions, depilatory creams and lotions, aftershave creams and lotions, tanning creams and lotions, haircare products, such as, for example, hairsprays, hair gels, hair setting lotions, hair rinses, permanent and semi permanent hair colorants, hair shaping compositions, such as cold waves and hair-smoothing compositions, hair tonics, hair creams and lotions, deodorants and antiperspirants, such as, for example, underarm sprays, roll-ons, deodorant sticks, deodorant creams, products in decorative cosmetics, such as, for example, eyeshadows, nail varnishes, foundations, lipsticks, mascara, and candles, lamp oils, joss-sticks, insecticides, repellents, propellants, compositions for oral care, in particular oral and/or tooth care agents such as toothpastes, tooth gels, tooth powders, mouthwashes, chewing gums and other oral care agents.

A particularly preferred embodiment according to the present invention is a product as defined above, wherein the product or the composition (ii) is selected from the group consisting of products from laundry care (e.g. softener, detergent, heavy duty detergent, liquid detergent, powder detergent, fabric (re)freshener, in-wash perfume, in-wash scent booster), home care (e.g. cleaner), air care (e.g. water-containing air freshener, air fresheners, electricals, membrane air freshener), personal care (e.g. creams, body lotion, shampoo, conditioner, shower gel, hair spray, sun protection lotions/sprays, deodorants), oral care (e.g. toothpaste, mouth waters), perfumery (e.g. EDT, EdC).

The present invention also relates to a method of producing a product as defined above, consisting of or comprising the following steps:

(I) providing a container (i) comprising or consisting of PE and/or PP and/or PET, preferably a container as defined above, (II) providing a composition (ii) as defined above, (III) filling the composition (ii) in the container (i), (IV) optionally, filling one or more further substances in the container, and (V) optionally, closing and/or sealing the container.

Preferred embodiments of the method according to the invention correspond to or can be derived from the preferred embodiments of the product according to the invention which are explained above.

The invention will now be described in more detail hereinafter with references to the examples. Further aspects of the present invention are disclosed in the accompanying claims.

EXAMPLES

Example 1

For the determination of the category and the behavior of the compounds, the influence of each compounds on the tree different plastic types LD-PE, PP and PET-G were investigated.

Plastic Items:

PET-G Polyethylene terephthalate glycol (Vivak, Rocholl GmbH)

PP Polypropylen (Simona DWST, Rocholl GmbH)

LD-PE Polyethylen with low density (Simona PEW, Rocholl GmbH)

Test Method:

Each plastic item of 13 mm×43 mm×2 mm was weighted and stored for 4 weeks at 40° C. in a 10 mL glass jar filled with a 10% solution of the single test compound in DPG. After the storage, the plastic item was taken out of the jar and carefully rinsed by dipping in ethanol. The rinsed plastic item was dabbed gently with a paper towel and immediately weighted. The weight of the plastic item before the storage and after the storage was compared and the percentage weight increase or decrease determined.

Furthermore the appearance of the plastic item was evaluated. The different evaluation qualities of the plastic items were classified as follows:

| evaluation quality | appearance of the plastic item |
|---|---|
| no change | no changes of the plastic item observed |
| colour change | plastic items was yellow or brown |
| opaque | plastic items was opaque |
| form change | plastic item was crooked |
| texture change | plastic item was sticky, soaked or porous |

Category A compounds showed a weight increase of 5 wt. % and more, and/or colour changes after 4 weeks at 40° C.

Category B compounds showed a weight increase in a range of from 2 wt. % to less than 5 wt. % and/or other changes of the appearance, like texture changes, form changes and opaque.

Category C compounds showed a weight increase of less than 2 wt. % and no changes of the appearance.

Table 1 below shows the results of several compounds and their assigned categories A and B, while the results of several compounds of category C are shown in table 2 below:

TABLE 1

Compound results of categories A and B

| | % Weight decrease/increase after 4 weeks at 40° C. | | | Appearance of the plastic after 4 weeks | | | |
|---|---|---|---|---|---|---|---|
| Category | LD-PE | PP | PET G | LD-PE | PP | PET G | Name |
| A | 10.2 | 2.4 | −0.2 | no change | no change | no change | CEDRENE |
| A | 5.5 | 5.6 | 0.3 | no change | form change | opaque | PHELLANDRENE L |
| A | 6 | 5.7 | 0.9 | no change | form change | opaque | LIMONENE D PURE |
| A | 5.2 | 5.6 | 0 | no change | texture change | opaque | MYRCENE |
| A | 1.5 | 0.3 | −0.2 | colour change | colour change | colour change | VERTOSINE |

TABLE 1-continued

| Compound results of categories A and B | | | | | | | |
|---|---|---|---|---|---|---|---|
| | % Weight decrease/increase after 4 weeks at 40° C. | | | Appearance of the plastic after 4 weeks | | | |
| Category | LD-PE | PP | PET G | LD-PE | PP | PET G | Name |
| A | 0.1 | 0.1 | 0.1 | colour change, form change | no change | no change | EUGENOL |
| B | 3.1 | 1.7 | 0 | no change | no change | no change | EUCALYPTOL |
| B | 4.4 | 2.5 | 3.6 | texture change | texture change | texture change | STYRENE |
| B | 1.8 | 2 | 2.1 | no change | no change | opaque | CRESYL METHYL ETHER PARA |
| B | 2 | 1.9 | 1 | no change | form change | opaque | HEXYL SALICYLATE |
| B | 0.6 | 0.4 | 1 | no change | no change | opaque | BENZYL BENZOATE M |
| B | 0.6 | 0.5 | 1 | form change | no change | opaque | CUMINIC ALDEHYDE |
| B | 0.2 | 0.4 | 1.3 | form change | no change | opaque | BENZYL ACETONE |
| B | 2 | 1.2 | 0 | no change | no change | no change | VERNALDEHYDE |
| B | 4.5 | 1 | −0.2 | no change | no change | no change | AMBERWOOD ® F |
| B | 4.1 | 0.4 | −0.3 | no change | no change | no change | YSAMBER ® K |
| B | 2.9 | 0.4 | −0.3 | no change | no change | no change | AMBROXIDE |

TABLE 2

| Compound results of category C | | | | | | | |
|---|---|---|---|---|---|---|---|
| | % Weight decrease/increase after weeks at 40° C. | | | Appearance of the plastic after 4 weeks | | | |
| Category | LD-PE | PP | PET G | LD-PE | PP | PET G | Name |
| C | 1.2 | 0.6 | 0 | no change | no change | no change | DYNASCONE |
| C | 1.5 | 0.3 | −0.2 | no change | no change | no change | ISO E SUPER |
| C | 1.7 | 0.2 | −0.2 | no change | no change | no change | ISOLONGIFOLANON |
| C | 1.5 | 0.9 | 0 | no change | no change | no change | CLARITONE ® |
| C | 1.4 | 0.2 | −0.2 | no change | no change | no change | AURELIONE ® |
| C | 1.6 | 0.3 | 0 | no change | no change | no change | GLOBANONE ® |
| C | 0.5 | 0.2 | −0.2 | no change | no change | no change | ISOBUTYL QUINOLINE DL |
| C | 1.2 | 1.5 | 1.4 | no change | no change | no change | PHENYLETHYL METHYL ETHER |
| C | 1.5 | 1.7 | 0.7 | no change | no change | no change | 2-ISOBUTYL-4-VINYL-1,3-DIOXOLANE |
| C | 0.6 | 0.2 | −0.2 | no change | no change | no change | DAMASCENONE |
| C | 1 | 1 | 0 | no change | no change | no change | LINALYL ACETATE |
| C | 0.1 | 0.2 | −0.2 | no change | no change | no change | LINALOOL |
| C | 0 | 0.1 | −0.2 | no change | no change | no change | CITRONELLOL 950 |
| C | 0 | 0.1 | −0.2 | no change | no change | no change | GERANIOL SUPER |
| C | 0 | 0.1 | −0.3 | no change | no change | no change | MAYOL |
| C | 1.1 | 0.8 | 0.1 | no change | no change | no change | HYACINTH BODY |
| C | 0.9 | 0.3 | 0 | no change | no change | no change | MAGNOLAN |
| C | 0.8 | 0.5 | 0.5 | no change | no change | no change | JACINTHAFLOR ® |
| C | 0.4 | 0.3 | 0.4 | no change | no change | no change | INDOFLOR ® |
| C | 0.2 | 0.1 | −0.2 | no change | no change | no change | CITRAL DIETHYL ACETAL |
| C | 0.1 | 0.2 | 0.6 | no change | no change | no change | HELIONAL |
| C | 0 | 0.1 | −0.2 | no change | no change | no change | PHENYLACETIC ACID |
| C | 0.2 | 0.1 | −0.3 | no change | no change | no change | BRAHMANOL ® |
| C | 0.2 | 0.2 | −0.4 | no change | no change | no change | MUGETANOL |
| C | 0 | 0.1 | −0.3 | no change | no change | no change | ALCOHOL C10 |
| C | 0 | 0 | −0.3 | no change | no change | no change | FURANEOL |
| C | 0.1 | 0 | −0.3 | no change | no change | no change | SANDALORE ® |
| C | 0 | 0 | 0 | no change | no change | no change | MAJANTOL ® |
| C | 0 | 0.1 | −0.3 | no change | no change | no change | SYMROSE ® |
| C | 0.6 | 0.5 | −0.2 | no change | no change | no change | ALDEHYDE C11 ISO |
| C | 0.4 | 0.4 | 0.3 | no change | no change | no change | STYRALYL ACETATE |
| C | 0 | 0 | −0.3 | no change | no change | no change | SYMFRESH ® NX |
| C | 0.5 | 0.5 | 0.3 | no change | no change | no change | CYCLOGALBANAT ® |
| C | 1.1 | 1.8 | 0.6 | no change | no change | no change | ETHYL BUTYRATE |
| C | 1.4 | 0.4 | −0.3 | no change | no change | no change | AGRUMEX HC |

TABLE 2-continued

| Compound results of category C | | | | | | | |
|---|---|---|---|---|---|---|---|
| | % Weight decrease/increase after weeks at 40° C. | | | Appearance of the plastic after 4 weeks | | | |
| Category | LD-PE | PP | PET G | LD-PE | PP | PET G | Name |
| C | 0.2 | 0.1 | 0 | no change | no change | no change | ETHYLENE BRASSYLATE |
| C | 1.2 | 1.2 | 0 | no change | no change | no change | UNDECANONE-2 |
| C | 1.1 | 0.3 | −0.3 | no change | no change | no change | KOAVONE |
| C | 0.9 | 0.2 | −0.2 | no change | no change | no change | TONALIDE |
| C | 0.8 | 0.3 | 0.7 | no change | no change | no change | NEROLIONE |
| C | 0 | 0 | −0.4 | no change | no change | no change | MALTOL |
| C | 1.8 | 0.3 | −0.2 | no change | no change | no change | AMBRETTOLIDE |
| C | 0.5 | 0.2 | 0 | no change | no change | no change | CANTRYL ® |
| C | 0.8 | 0.8 | 0 | no change | no change | no change | OZONIL |

Example 2

Perfume Composition A

TABLE 3

| Perfume composition A | | | | | | |
|---|---|---|---|---|---|---|
| Water Solubility calc. [mg/L] | Name | IUPAC name | Mass Molar [g/mol] | Mol. formula | Mol. structure | g/100 g |
| 0.1504 | CEDRENE | (1S,2R,5S)-2,6,6,8-Tetramethyltricyclo [5.3.1.01.5] undec-8-ene | 204 | $C_{15}H_{24}$ | 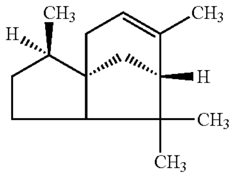 | 0.0006 |
| 2.862 | PHELLAN-DRENEL | 5-isopropyl-2-methyl-cyclohexa-1,3-diene | 136 | $C_{10}H_{16}$ | 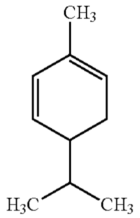 | 0.0619 |
| 3.2 | LIMONENE | 4-isopropenyl-1-methyl-cyclohexene | 136 | $C_{10}H_{16}$ | 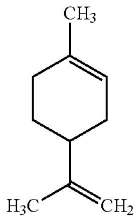 | 0.1238 |
| 6.9 | MYRCENE | 7-methyl-3-methylene-octa-1,6-diene | 136 | $C_{10}H_{16}$ | 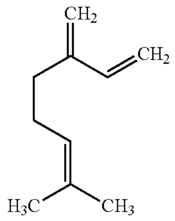 | 0.0619 |

TABLE 3-continued

| Perfume composition A | | | | | | |
|---|---|---|---|---|---|---|
| Water Solubility calc. [mg/L] | Name | IUPAC name | Mass Molar [g/mol] | Mol. formula | Mol. structure | g/100 g |
| 1.3 | VERTOSINE | methyl 2-[(E)-(2,4-dimethylcyclohex-3-en-1-yl) methyleneamino] benzoate | 271 | $C_{17}H_{21}NO_2$ | 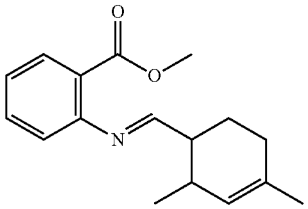 [SMILES: COC(=O)c1ccccc1/N=C/C1CCC(C)=CC1C] | 0.0001 |
| 754 | EUGENOL | 4-allyl-2-methoxy-phenol | 164 | $C_{10}H_{12}O_2$ | 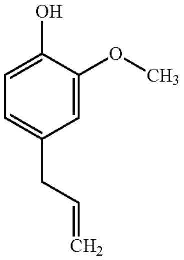 | 0.0309 |
| 532.4 | EUCALYPTOL | 2,2,4-trimethyl-3-oxabicyclo[2.2.2] octane | 154 | $C_{10}H_{18}O$ | 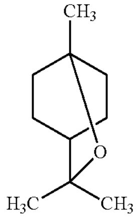 | 0.9283 |
| 343.7 | STYRENE | styrene | 104 | $C_8H_8$ | 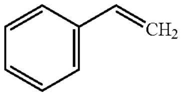 | 0.0006 |
| 527.1 | CRESYL METHYL ETHER PARA | 1-methoxy-4-methyl-benzene | 122 | $C_8H_{10}O$ | 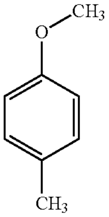 | 0.0006 |
| 6.1 | HEXYL SALICYLATE | hexyl 2-hydroxybenzoate | 222 | $C_{13}H_{18}O_3$ | 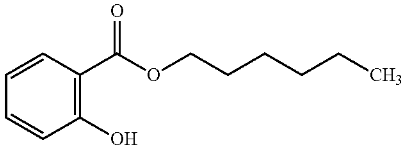 [SMILES: CCCCCCOC(=O)c1ccccc1O] | 1.8566 |
| 15.4 | BENZYL BENZOATE M | benzyl benzoate | 212 | $C_{14}H_{12}O_2$ | 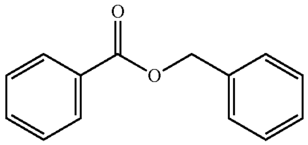 [SMILES: O=C(OCc1ccccc1)c1ccccc1] | 0.0062 |

TABLE 3-continued

| Perfume composition A | | | | | | |
|---|---|---|---|---|---|---|
| Water Solubility calc. [mg/L] | Name | IUPAC name | Mass Molar [g/mol] | Mol. formula | Mol. structure | g/100 g |
| 152.8 | CUMINIC ALDEHYDE | 4-isopropyl-benzaldehyde | 148 | $C_{10}H_{12}O$ | 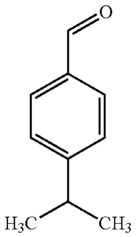 | 0.0062 |
| 1625 | BENZYL ACETONE | 4-phenylbutan-2-one | 148 | $C_{10}H_{12}O$ | 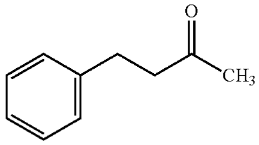 | 0.0062 |
| 1.2 | VERNALDE-HYDE | 4-isohexyl-1-methyl-cyclohex-3-ene-1-carbaldehyde | 208 | $C_{14}H_{24}O$ | 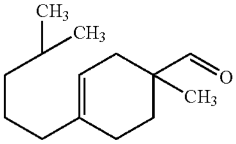 | 0.3094 |
| 0.5 | AMBER-WOOD ® F | ethoxymethoxy-cyclododecane | 242 | $C_{15}H_{30}O_2$ | 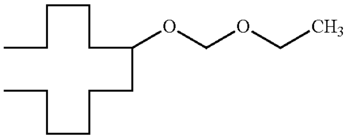 [SMILES: CCCCCCC(CCCCC)OCOCC] | 0.0619 |
| 0.1 | YSAMBER ® K | 2',2',8',8'-tetramethylspiro (1,3-dioxolane-2,10'-octahydro-1H-2,4a-methan-onapthalene) | 264 | $C_{17}H_{28}O_2$ | 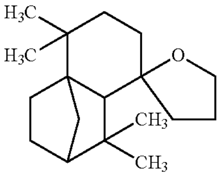 [SMILES: CC1(C)C2CCC3(C2)C1C1(CCCO1)CCC3(C)C] | 0.0006 |
| 2.4 | AMBROXIDE | (3aS,5aR,9aR)-3a,6,6,9a-tetramethyl-2,4,5,5a,7,8,9,9b-octahydro-1H-benzo[e] benzofuran | 236 | $C_{16}H_{28}O$ | 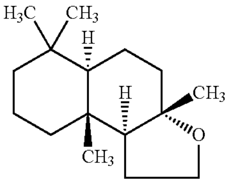 | 0.0062 |
| 7.6 | DYNASCONE | 1-(5,5-dimethylcyclohexen-1-yl)pent-4-en-1-one | 192 | $C_{13}H_{20}O$ | 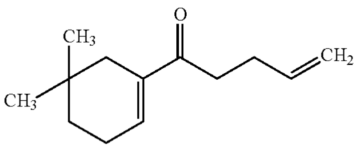 | 0.3094 |
| 1.1 | ISO E SUPER | 1-[(2R,3R)-2,3,8,8-tetramethyl-1,3,4,5,6,7-hexahydro-naphthalen-2-yl]ethanone | 234 | $C_{16}H_{26}O$ | 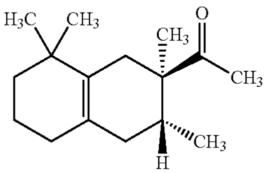 [SMILES: CC(=O)[C@]1(C)CC2=C(CCCC2(C)C)C[C@H]1C] | 3.0943 |

TABLE 3-continued

| Perfume composition A | | | | | | |
|---|---|---|---|---|---|---|
| Water Solubility calc. [mg/L] | Name | IUPAC name | Mass Molar [g/mol] | Mol. formula | Mol. structure | g/100 g |
| 21.1 | ISOLONGI-FOLANON | 2,2,8,8-tetramethyl-octahydro-1H-2,4a-methanonapthalene-10-one | 220 | $C_{15}H_{24}O$ | 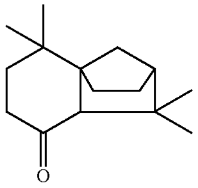 [SMILES: CC1(C)C2CCC3(C2)C1C(=O)CCC3(C)C] | 0.0619 |
| 28.1 | CLARITONE ® | 2,4,4,7-tetramethyloct-6-en-3-one | 182 | $C_{12}H_{22}O$ | 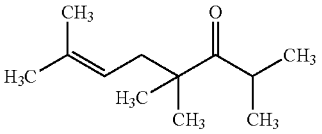 | 0.0619 |
| 0.3 | AURELIONE ® | (8E)-cyclohexadec-8-en-1-one | 236 | $C_{16}H_{28}O$ | 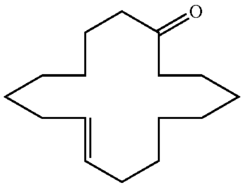 [SMILES: O=C1CCCCCC/C=C/CCCCCCC1] | 0.9283 |
| 0.3 | GLOBANONE ® | (8E)-cyclohexadec-8-en-1-one | 236 | $C_{16}H_{28}O$ | 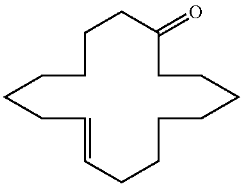 [SMILES: O=C1CCCCCC/C=C/CCCCCCC1] | 0.9283 |
| 16.7 | ISOBUTYL QUINOLINE DL | 7-isobutylquinoline | 185 | $C_{13}H_{15}N$ | 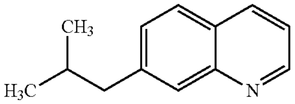 | 0.0006 |
| 1008 | PHENYLETHYL METHYL ETHER | 2-methoxyethyl-benzene | 136 | $C_9H_{12}O$ | 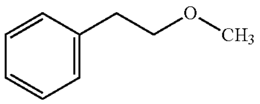 | 1.2377 |
| 800.3 | 2-ISOBUTYL-4-VINYL-1,3-DIOXOLANE | 2-isobutyl-4-vinyl-1,3-dioxolane | 156 | $C_9H_{16}O_2$ | 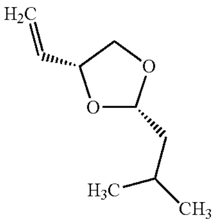 | 0.6189 |
| 12.48 | DAMASCENONE | (E)-1-(2,6,6-trimethylcyclohexa-1,3-dien-1-yl)but-2-en-1-one | 190 | $C_{13}H_{18}O$ | 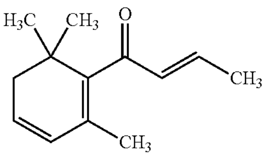 | 3.0943 |

TABLE 3-continued

| Perfume composition A | | | | | | |
|---|---|---|---|---|---|---|
| Water Solubility calc. [mg/L] | Name | IUPAC name | Mass Molar [g/mol] | Mol. formula | Mol. structure | g/100 g |
| 0.5 | AMBER-WOOD ® F | ethoxymethoxy-cyclododecane | 242 | $C_{15}H_{30}O_2$ | 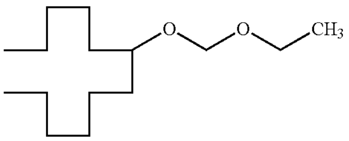 | 0.0619 |
| 8.2 | LINALYL ACETATE | (1,5-dimethyl-1-vinyl-hex-4-enyl) acetate | 196 | $C_{12}H_{20}O_2$ | 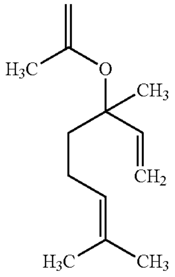 | 9.2829 |
| 683.7 | LINALOOL | 3,7-dimethylocta-1,6-dien-3-ol | 154 | $C_{10}H_{18}O$ | 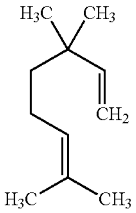 | 6.1886 |
| 211.8 | CITRONELLOL 950 | 3,7-dimethyloct-6-en-1-ol | 156 | $C_{10}H_{20}O$ | 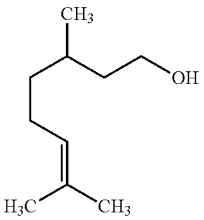 | 3.0943 |
| 255.8 | GERANIOL SUPER | (2E)-3,7-dimethylocta-2,6-dien-1-ol | 154 | $C_{10}H_{18}O$ | 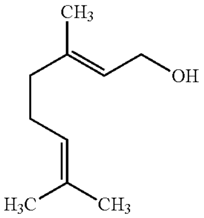 | 15.4714 |
| 258.2 | MAYOL | (4-isopropyl-cyclohexyl) methanol | 156 | $C_{10}H_{20}O$ | 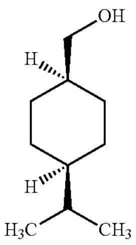 | 0.0619 |
| 152.3 | HYACINTH BODY | 2-(1-ethoxyethoxy) ethylbenzene | 194 | $C_{12}H_{18}O_2$ | 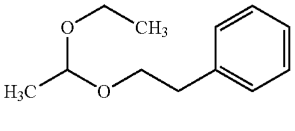 | 0.0619 |

TABLE 3-continued

| Perfume composition A | | | | | | |
|---|---|---|---|---|---|---|
| Water Solubility calc. [mg/L] | Name | IUPAC name | Mass Molar [g/mol] | Mol. formula | Mol. structure | g/100 g |
| 217.1 | MAGNOLAN | (2R,4R,4aS,9bR)-2,4-dimethyl-4,4a,5,9b-tetrahydroindeno [1,2-d][1,3]dioxine | 204 | $C_{13}H_{16}O_2$ | 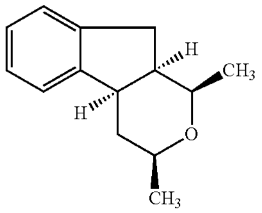 | 0.0062 |
| 2119 | JACINTHA-FLOR ® | (2R,4S)-2-methyl-4-phenyl-1,3-dioxolane | 164 | $C_{10}H_{12}O_2$ | 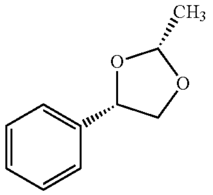 | 0.0006 |
| 1549 | INDOFLOR ® | 4,4a,5,9b-tetrahydroindeno [1,2-d][1,3]dioxine | 176 | $C_{11}H_{12}O_2$ | 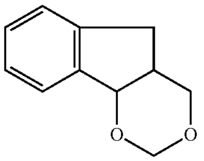 [SMILES: c1ccc2c(c1)CC1COCOC21] | 0.0006 |
| 2.5 | CITRAL DIETHYL ACETAL | (2E)-1,1-diethoxy-3,7-dimethyl-octa-2,6-diene | 226 | $C_{14}H_{26}O_2$ | 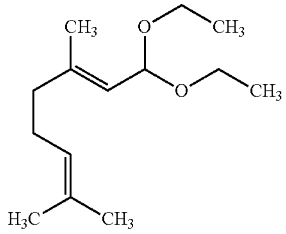 [SMILES: CCOC(/C=C(\C)CCC=C(C)C)OCC] | 0.0619 |
| 342.6 | HELIONAL | 3-(1,3-benzodioxol-5-yl)-2-methyl-propanal | 192 | $C_{11}H_{12}O_3$ | 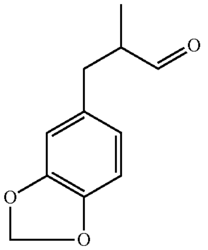 | 0.0619 |
| 13500 | PHENYLACETIC ACID | 2-phenylacetic acid | 136 | $C_8H_8O_2$ | 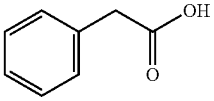 | 6.1886 |
| 13.5 | BRAHMANOL ® | 2-methyl-4-(2,2,3-trimethylcyclopent-3-en-1-yl)butan-1-ol | 196 | $C_{13}H_{24}O$ | 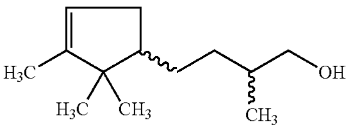 | 0.0062 |

TABLE 3-continued

| Water Solubility calc. [mg/L] | Name | IUPAC name | Mass Molar [g/mol] | Mol. formula | Mol. structure | g/100 g |
|---|---|---|---|---|---|---|
| Perfume composition A | | | | | | |
| 97.8 | MUGETANOL | 1-(4-isopropylcyclohexyl) ethanol | 170 | $C_{11}H_{22}O$ | 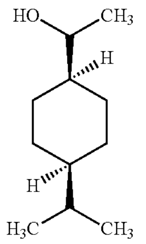 | 0.0619 |
| 28.2 | ALCOHOL C10 | decan-1-ol | 158 | $C_{10}H_{22}O$ | 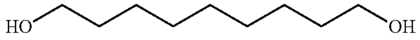 [SMILES: OCCCCCCCCCO] | 0.3094 |
| 18500 | FURANEOL | 4-hydroxy-2,5-dimethyl-furan-3-one | 128 | $C_6H_8O_3$ | 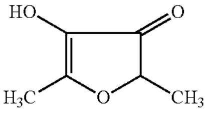 | 0.062 |
| 5 | SANDALORE ® | 3-methyl-5-(2,2,3-trimethylcyclopent-3-en-1-yl)pentan-2-ol | 210 | $C_{14}H_{26}O$ | 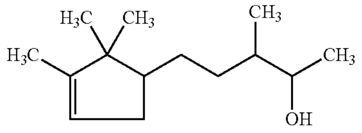 | 0.0062 |
| 195.3 | MAJANTOL ® | 2,2-dimethyl-3-(m-tolyl)propan-1-ol | 178 | C12H18O | 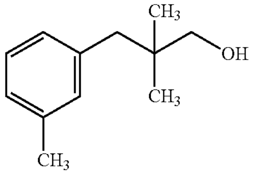 | 0.0619 |
| 84.67 | SYMROSE ® | 4-isopentylcyclohexanol | 170 | $C_{11}H_{22}O$ | 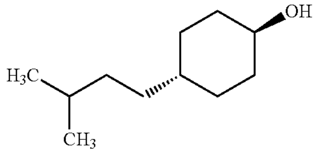 | 0.9283 |
| 22.3 | ALDEHYDE C11 ISO | (E)-undec-9-enal | 168 | $C_{11}H_{20}O$ | 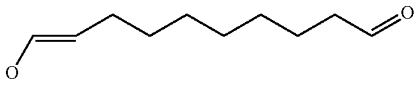 [SMILES: O=CCCCCCCC/C=C/O] | 9.2829 |
| 481.1 | STYRALYL ACETATE | 1-phenylethyl acetate | 164 | $C_{10}H_{12}O_2$ | 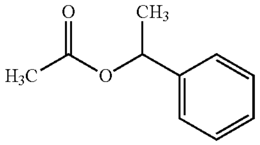 | 6.1886 |
| 321.5 | SYMFRESH ® NX | (3-hydroxy-2,2,4-trimethyl-pentyl) 2-methylpropanoate | 216 | $C_{12}H_{24}O_3$ | 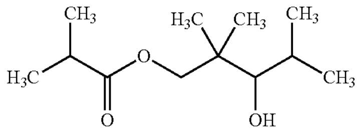 | 3.0943 |
| 211.1 | CYCLO-GALBANAT ® | allyl 2-(cyclohexoxy) acetate | 198 | $C_{11}H_{18}O_3$ | 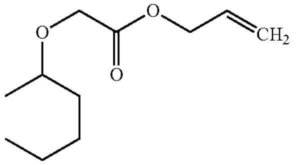 | 0.0619 |

TABLE 3-continued

| Perfume composition A | | | | | | |
|---|---|---|---|---|---|---|
| Water Solubility calc. [mg/L] | Name | IUPAC name | Mass Molar [g/mol] | Mol. formula | Mol. structure | g/100 g |
| 2745 | ETHYL BUTYRATE | ethyl butanoate | 116 | $C_6H_{12}O_2$ | 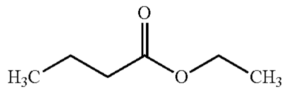 | 1.8566 |
| 7.5 | AGRUMEX HC | [(1S,2S)-2-tert-butylcyclohexyl] acetate | 198 | $C_{12}H_{22}O_2$ | 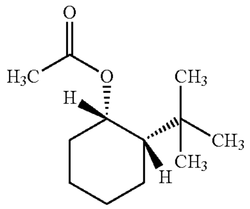 | 9.2829 |
| 0.1 | ETHYLENE BRASSYLATE | 1,4-dioxacyclo-heptadecane-5,17-dione | 270 | $C_{15}H_{26}O_4$ | 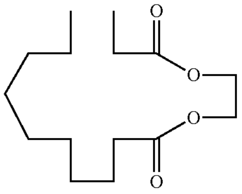 [SMILES: CCCCCCCCCC(=O)OCCOC(=O)CC] | 3.0943 |
| 19.7 | UNDECANONE-2 | undecan-2-one | 170 | $C_{11}H_{22}O$ | 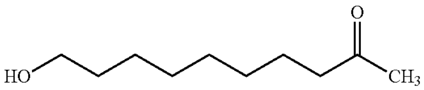 | 0.0619 |
| 14.3 | KOAVONE | (E)-3,4,5,6,6-pentamethylhept-3-en-2-one | 182 | $C_{12}H_{22}O$ | 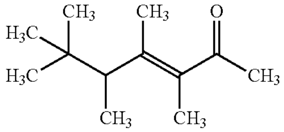 | 0.0619 |
| 0.1 | TONALIDE | 1-(1,1,2,4,4,7-hexamethyltetralin-6-yl)ethanone | 258 | $C_{18}H_{26}O$ | 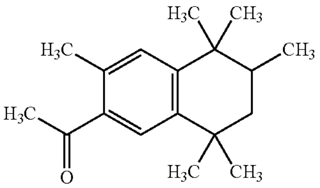 [SMILES: CC(=O)c1cc2c(cc1C)C(C)(C)C(C)CC2(C)C] | 0.0006 |
| 414.7 | NEROLIONE | 1-(3-methylbenzofuran-2-yl)ethanone | 174 | $C_{11}H_{10}O_2$ | 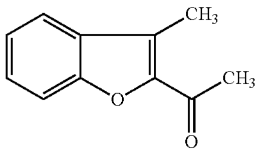 | 0.9283 |
| 79800 | MALTOL | 3-hydroxy-2-methyl-pyran-4-one | 126 | $C_6H_6O_3$ | 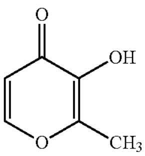 | 0.0062 |

TABLE 3-continued

Perfume composition A

| Water Solubility calc. [mg/L] | Name | IUPAC name | Mass Molar [g/mol] | Mol. formula | Mol. structure | g/100 g |
|---|---|---|---|---|---|---|
| 0.6 | AMBRETTOLIDE | (10E)-1-oxacycloheptadec-10-en-2-one | 252 | $C_{16}H_{28}O_2$ | 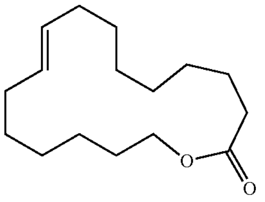 [SMILES: O=C1CCCCCCC/C=C/CCCCCCO1] | 0.9283 |
| 59.8 | CANTRYL ® | 2-(2,2,3-trimethylcyclopent-3-en-1-yl) acetonitrile | 149 | $C_{10}H_{15}N$ | 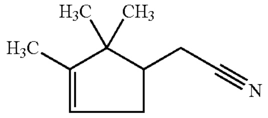 | 0.0062 |
| 1.3 | OZONIL | (E)-tridec-2-enenitrile | 193 | $C_{13}H_{23}N$ | 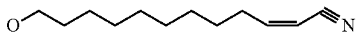 [SMILES: N#C/C=C\CCCCCCCCCO] | 0.0062 |
| — | DPG | — | 134 | $C_5H_{14}O_3$ | — | 9.2829 |
| 7.37 | IPM | Isopropyl tetradecanoate | 270 | $C_5H_{12}O_2$ | 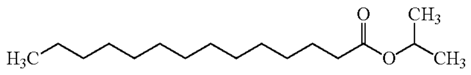 | 0.0619 |
| 1.17 | TEC | ethyl citrate | 276 | $C_{12}H_{20}O_7$ | 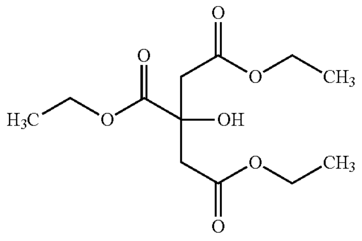 [SMILES: CCOC(=O)CC(O)(CC(=O)OCC)C(=O)OCC] | 0.681 |
| — | Pentanediol | 1,2-pentanediol | 104 | $C_5H_{12}O_2$ | 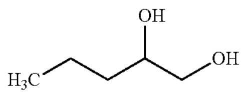 | 0.0309 |
| — | Symsave H | 4-hydroxy-acetophenone | 136 | $C_5H_{12}O_2$ | 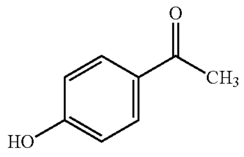 | 0.0062 |
| — | Propanediol | 1,2-Propanediol | 76 | $C_3H_8O_2$ | 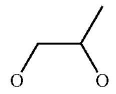 | 0.0309 |
| | | | | | Sum | 100.0000 |

Example 3

Softener

| Material | Manufacturer | Chemical name | wt.-% |
|---|---|---|---|
| Deoinised water | | Water | 72.4 |
| Rewoquat WE 18 | Evonic Goldschmidt GmbH | Dialkylesterammon-iumethosulfate | 16.6 |
| Mergal K9N | Honeywell Austria GmbH | 5-Chloro-2-methyl-3-(2H)-isothiazolone and 2-methyl-3-(2H)-isothiazolone | 0.10 |
| Dow Corning 1520 Antifoam | Dow Corning GmbH, Germany | Polydimethyl siloxane | 0.30 |
| Magnesium chloride 1% solution | — | Magnesium chloride solution | 10.00 |
| Perfume composition A | Symrise | — | 0.60 |

Example 4

Soap

| Material | Manufacturer | Chemical name | wt.-% |
|---|---|---|---|
| Deionised water | | Water | 2.0 |
| Soap Base Mix | diverse | Sodium tallowates/ palmitates | 96.95 |
| Titandioxid | Kronos Titan GmbH, Deutschland | Titanium Dioxide | 1.0 |
| Perfume composition A | Symrise | | 1.5 |

Example 5

Powder Detergent

| Material | Manufacturer | Chemical name | wt.-% |
|---|---|---|---|
| Natrium Metasilicat Pentahydrate | Akzo Nobel Chemicals, Deutschland | Sodium Metasilicate Pentahydrate | 48.0 |
| Natriumhydrogen-carbonate | diverse | Sodium hydrogen carbonate | 15.0 |
| Natriumpercarbonat | diverse | Sodium carbonate peroxyhydrate | 15.0 |
| Peractive AC Blue | Clariant GmbH, Deutschland | TAED/Na-Carboxymethylcellulose | 5.00 |
| Genapol OA-080 | Clariant GmbH, Deutschland | Oxoalkohol C14-15, 8EO | 3.00 |
| Texapon K12 Pulver | Cognis Deutschland GmbH | Sodium Lauryl Sulphate C12 | 7.00 |
| Tinopal CBS-X | Ciba, Deutschland | | 0.50 |
| Savinase 6.0 T, Type W | Novozymes | Protease | 0.40 |

Example 6

Cleaner, Liquid

| Material | Manufacturer | INCI | wt.-% |
|---|---|---|---|
| Demineralized water | | aqua | 93.2 |
| Kelzan ASX-T | CP Kelco Germany GmbH | Xanthan gum | 0.5 |
| HOESCH NAS 60 | Hoesch Julius | Sulfonic acid, C13-17-sec-Alkyl-, sodium salt | 1.0 |
| Citric acid | Symrise | Citric acid | 5.0 |
| Perfume composition A | | Parfum | 0.3 |
| Sum | | | 100.00 |

Heat water to about 35° C. Sprinkle kelzan onto water while stirring and maintain agitation for another 30 min. to complete hydration. Add and dissolve the remaining components in the given order. Use of either blade or propeller mixer should yield good results.

Example 7

Make-Up Remover

| Material | INCI | wt.-% |
|---|---|---|
| Phase A | | |
| Glycerin | Glycerin | 9.30 |
| Surfhope ® C-1216 | Sucrose Laurate | 3.00 |
| Surfhope ® C-1616 | Sucrose Palmitate | 3.00 |
| Water | Water (Aqua) | 4.70 |
| Phase B | | |
| Neutral oil | Caprylic/Capric Triglyceride | 48.71 |
| Dragoxat ® 89 | Ethylhexyl Isononanoate | 30.00 |
| lonol CP | BHT | 0.05 |
| Phase C | | |
| Symdiol ® 68 | 1,2-Hexanediol, Caprylyl Glycol | 0.80 |
| Phase D | | |
| Perfume composition A | Parfum | 0.15 |
| Colour system I | Colour | 0.15 |
| Colour system II | Colour | 0.14 |
| Sum | | 100.00 |

The production takes place in a Becomix.

For production of phase A, the glycerin and Surfhope® C1216 are put into the Becomix and are stirred at −0.5 bar with 0.3 m/s, then they are homogenized with the aid of a Turrax at 3 m/s for 4 minutes. When the Surf Hope® C1216 is completely dissolved, the Surf Hope® C1616 is added, whereby the stirring is continued at 0.3 m/s. The subsequent homogenization takes place at 3 m/s for 4 minutes with the aid of a Turrax. Then water is added and again homogenized with the aid of a Turrax at 3 m/s for 6 minutes. This mixture is heated to 80° C. under stirring at 0.3 m/s, then brought to 50° C. and again homogenized with the aid of a Turrax with 3 m/s for 2 minutes. Subsequently, the temperature is raised to 80° C. and a pressure of −0.6 bar is adjusted.

The production of phase B takes place at 80° C. At a temperature of 80° C., the components of phase B are very slowly and consecutively mixed with each other and then stirred at 0.5 m/s as well as homogenized with the aid of a Turrax at 3 m/s for 2 minutes. When one quarter of the oil has been put into the boiler, a homogenization step takes place with the aid of a Turrax at 5 m/s for 4 minutes. After half of the oil has been added, it is homogenized again with the aid of a Turrax at 5 m/s for 4 minutes and the stirring speed is raised to 0.8 m/s. When three quarters of the oil have been added, a homogenization step with the aid of a Turrax at 5 m/s for 4 minutes and an increase of the stirring speed to 1 m/s follow. Then the remaining amount of the oil is added and stirred at 1.2 m/s.

After addition of phase C, the pressure is raised to −0.8 bar and it is homogenized with the aid of a Turrax at 5 m/s for 4 minutes. The preparation is cooled under stirring at 0.5 m/s to 25° C., whereby the stirring speed is reduced. Then phase D is added at 40° C.

Colour system I: 0.1% solution in isopropyl palmitate of D&C Red N °17 C.I. 26100

Colour system II: 0.1% solution in isopropyl palmitate of Phat Brown DC 8206: C.I. 47000, C.I. 26100, C.I. 60725

The final preparation has a viscosity of 69280 cP.

Example 8

Shampoo

| Material | INCI | wt.-% |
|---|---|---|
| Water | Water | 71.3000 |
| Citric acid | Citric acid | 0.1000 |
| Euperlan PK 771 | Glycol Distearate, Sodium Laureth Sulfate, Cocamide MEA, Laureth-10 | 6.0000 |
| Sodium Chloride | Sodium Chloride | 1.4000 |
| Plantacare PS 10 | Sodium Laureth Sulfate, Lauryl Glucoside | 20.0000 |
| Preservative | | 0.5000 |
| Perfume composition A | Perfume | 0.7000 |
| Sum | | 100.0000 |

In the tank, at room temperature introduce all the ingredients in the listed order while stirring until homogenization. If necessary, adjust the pH to 6 with citric acid or sodium hydroxide.

Example 9

Lip Care Stick

| Component | INCI | wt.-% |
|---|---|---|
| Medium mineral oil | Paraffinium Liquidum | 26.00 |
| Permulgin 3220 | Ozokerite | 20.00 |
| Paraffin 52-54 | Paraffin | 12.00 |
| Neutral oil | Caprylic/Capric Triglyceride | 10.00 |
| Prisorine Sqs 3758 | Hydrogenated Polyisobutene | 5.00 |
| Cetiol 868 | Ethylhexyl Stearate | 5.00 |
| Softisan 100 | Hydrogenated Cocoglycerides | 5.00 |
| Xiameter ® PMX-0245 Cyclosiloxane | Cyclopentasiloxane | 4.00 |
| Elfacos E 200 | Methoxy PEG-22 and Dodecyl Glycol Copolymer | 4.00 |
| Permulgin 3430 | *Copernicia Cerifera* (Carnauba) Wax | 2.00 |

-continued

| Component | INCI | wt.-% |
|---|---|---|
| Ivarlan 3360 | Glyceryl Lanolate | 3.00 |
| Super Hartolan | Lanolin Alcohol | 1.40 |
| Cutina ® FS 45 | Stearic acid, Palmitic acid | 1.50 |
| Jojoba oil | | 1.00 |
| Titanium dioxide | Titanium Dioxide | 0.10 |
| Perfume composition A | Perfume | 0.01 |
| Sum | | 100.00 |

For production, all of the components in the order of the list without the perfume are melted and homogenized during warming to 70° C. At a temperature of 50° C., the perfume is added and homogenized.

Example 10

Dishwash, Liquid Manual

| Component | | INCI | wt.-% |
|---|---|---|---|
| Water, demin. | | Water (aqua) | 41.7 |
| Glucopon 650 EC | BASF | Coco Glucoside | 4.0 |
| Zetesol NL-2 | Zschimmer & Schwarz | Sodium Laureth sulfate | 45.0 |
| Dehyton AB 30 | BASF | Coco-Betaine | 8.0 |
| Ethanol 96% | Symrise | Ethanol | 1.0 |
| Parmetol MBX | Hoesch Julius | Benzisothiazolinone, Methylisothiazolinone, Laurylamine Dipropylenediamine | 0.1 |
| Perfume composition A | Symrise | Perfume | 0.2 |
| Sum | | | 100.00 |

Mix ingredient 1 to 7 in the given order. Make sure that each ingredient is completely solved before adding the next. Adjust pH-value with citric acid.

Example 11

Night Cream

| Component | INCI | wt.-% |
|---|---|---|
| Phase A | | |
| Dragosan W/O P | Sorbitan Isostearate, Hydrogenated Castor oil, Beeswax (Cera Alba) | 5.00 |
| Medium Mineral Oil | Paraffinium Liquidum | 15.00 |
| Vaseline | Petrolatum | 4.50 |
| Tece Ozokerit N 325/II | Ozokerite | 2.30 |
| Dragoxat ® 89 | Ethylhexyl Isononanoate | 5.00 |
| Phase B | | |
| Water | Water (Aqua) | 64.60 |
| Glycerin, 99.5 P. | Glycerin | 3.00 |
| Magnesiumsulfate Heptahydrate | Magnesium Sulfate | 0.70 |
| Preservative Complex (ND Liquid) | Triethylene Glycol, Imidazolidinyl Urea, Methylparaben, Propylparaben, Dehydroacetic acid | 0.30 |
| Phase C | | |
| Perfume composition A | Perfum | 0.10 |
| Sum | | 100.00 |

For production, phase A and phase B are separately warmed to 80° C., respectively. Then phase B is added to phase A while using an Ultra-Turrax and emulsified. While stirring with a paddle agitator, this mixture is cooled and then emulsified again at 60° C. When the mixture has reached a temperature of about 35° C., phase C is added.

Example 12

Liquid Soap

| Material | INCI | wt.-% |
|---|---|---|
| water | Water | 77.4360 |
| Plantacare PS 10 | Sodium Laureth sulfate, Lauryl Glucoside | 20.0000 |
| Preservative | | 0.5000 |
| Sodium chloride | Sodium Chloride | 1.4000 |
| Citric acid monohydrate | Citric Acid | 0.1640 |
| Perfume composition A | Perfume | 0.5000 |
| Sum | | 100.0000 |

In the tank, at room temperature introduce all the ingredients in the listed order while stirring until homogenization. If necessary, adjust the pH with citric acid or sodium hydroxide to a final pH of 6.

Example 13

Detergent Soap Bar

| material | INCI | wt.-% |
|---|---|---|
| Britesil H 20 | Sodium Silicate | 14.6500 |
| Dolomite | Sudesan | 25.0000 |
| Basic soap HTS | Sodium Tallowate, sodium Cocoate, sodium Palm Kernelate | 45.0000 |
| Marlon ARL | C-10-13, ABS-Na, Powder | 6.7000 |
| Texapon Z HK Powder | Sodium fatty alcohol C12-C18 | 6.6000 |
| Titanium dioxide | Titanium dioxide | 1.0000 |
| Color Acid blue 7, C.I.42080 Powder | | 0.2000 |
| Perfume composition A | Perfume | 0.8500 |
| Sum | | 100.0000 |

Example 14

Dishwashing Liquid

| material | INCI | Gew.-% |
|---|---|---|
| Water, demineralisiert | Water | 41.8000 |
| Glucopon 650 EC | Coco Glucoside | 4.0000 |
| Zetesol NL-2 | Sodium Laureth Sulfate | 45.0000 |
| Dehyton AB 30 | Coco-Betaine | 8.0000 |
| Ethanol 96% | Ethanol | 1.0000 |
| Parmatol MBX | Benisothiazolinone, Methylisothiazolinone, Laurylamine, Dipropylenediamine | 0.1000 |
| Perfume composition A | Perfume | 0.1000 |
| Sum | | 100.0000 |

Mix all ingredients in the given order. Make sure that each ingredient is completely solved before adding the next. Adjust the pH-value with citric acid to pH value of 7.

Example 15

Hair Conditioner

| Material | INCI | wt.-% |
|---|---|---|
| Phase A | | |
| Hostaphat Kw 340 D | Trieteareth-4 Phospate | 10.0000 |
| Medium Mineral Oil | Paraffinium Liquidum | 6.0000 |
| Lunacera M | Ozocerite | 5.0000 |
| Isopropylmyristate | Isopropyl myristate | 5.0000 |
| Xiameter ® PMX-200 Silicone Fluid | Dimethicone | 0.5000 |
| Lanolin Alcohol | Lanolin Alcohol | 0.5000 |
| Phase B | | |
| Water | Water (Aqua) | 29.1000 |
| Preservative | | 0.8000 |
| Glycerin, 99.5 P. | Glycerin | 12.0000 |
| Citric acid 20% aqu. Solution | Citric acid | 1.3000 |
| Phase C | | |
| Water | Water (Aqua) | 28.9000 |
| Carbopol ® Ultrez-10 | Caromer | 0.2000 |
| Triethanolamin 99% | Triethanolamine | 0.3000 |
| Phase D | | |
| Perfume composition A | Perfume | 0.4000 |
| Sum | | 100.0000 |

Phase A: Mix and heat all ingredients of phase A to 75° C.

Phase B: Heat the water at 80° C., add the rest of phase B. Homogenize. Add the phase A to B stirring.

Phase C: Swell Ultrez 10 in water with strong stirring. Add Triethanolamine to obtain a limpid gel.

Example 16

Detergent, Liquid, Heavy Duty

| Material | INCI | wt.-% |
|---|---|---|
| 1 Water | Water | 39.7000 |
| 2 Tinopal CBS-X | Disodium Distyrylbiphenyl Disulfonate | 0.1000 |
| 3 Edenor K 12-18 | Cocos fatty acids | 7.5000 |
| 4 Potassium hydroxide 50% solutio | Potassium Hydroxide | 4.3000 |
| 5 Propylene glycol 1,2 | Propan-1,2-diol | 5.0000 |
| 6 Hoesch T 9 90% | Trideceth-9 | 12.0000 |
| 7 Parmatol A 26 | Mixture of 5-Chloro-2-methyl-2H-isothiazol-3-one and 2-Methyl-2H-isothiazol-3-one | 0.2000 |
| 8 Hoesch NAS 60 | Sulfonic acid, C 13-17-sec-Alkyl-, Sodium salt | 17.0000 |
| 9 Triethanolamine pure C | Triethanolamine | 2.0000 |
| 10 Trisodium citrate dihydrat | Tri-sodiumcitrate-dihydrate | 5.0000 |
| 11 Hoesch Phos DET 32 D | Diethylenetriamine Pentamethylene Phosphonic acid Sodium salt | 3.0000 |
| 12 Ethanol 96% | Ethanol | 3.0000 |
| 13 Alcalase 2.5 L | Protease | 0.4000 |
| 14 Termamyl 300L | Alpha-Amylase | 0.3000 |
| 15 Perfume composition A | Perfume | 0.5000 |
| Sum | | 100.0000 |

Mix ingredients 1 and 2. Heat up to 50° C. Add ingredient 3 and 4, stir until soap has formed. Add ingredients 5 to 10 in the given order. Cool down to 30° C.

Add ingredients 11 to 14 in the given order. Adjust pH to 8.5, if necessary.

Example 17

Detergent, Liquid

| material | INCI | wt.-% |
|---|---|---|
| 1 Water, demineralized | Water | 48.3000 |
| 2 Edenor K 12-18 | Cocos fatty acids | 3.0000 |
| 3 Sodium hydroxide 50% solution | Sodium Hydroxide | 2.5000 |
| 4 Novethix L-10 Polymer | NRC Nordmann, Rassmann | 2.5000 |
| 5 Zetesol NL-2 | Sodium Laureth Sulfate | 30.0000 |
| 6 Hoesch AE 50 | sodium Dodecylbenzenesulfonate | 3.0000 |
| 7 Dehydol LT 7 | | 3.0000 |
| 8 Hoesch Phos DET 32 D | Diethylenetriamine Pentamethylene Phosphonic acid Sodium salt | 1.0000 |
| 9 Ethanol 96% | Ethanol | 2.0000 |
| 10 Propylene glycol 1,2 | Propan-1,2-diol | 2.0000 |
| 11 Trisodium citrate dihydrat | Tri-sodiumcitrate-dihydrate | 2.0000 |
| 12 Perfume composition A | Perfume | 0.5000 |
| 13 Parmatol A 26 | Mixture of 5-Chloro-2-methyl-2H-isothiazol-3-one and 2-Methyl-2H-isothiazol-3-one | 0.2000 |
| Sum | | 100.0000 |

Add all other ingredients in the given order. Make sure that every ingredient is solved before adding the next. If it is necessary, adjust pH to 9 with citric acid.

Example 18

Transparent Deo-Stick (A) & Cream-Deo-Stick (B)

| material | A wt.-% | B wt.-% |
|---|---|---|
| Water, demineralized | 36.5500 | 54.8500 |
| Aluminium Zirconium Tetrachlorohydrate-Glycin Komplex | 25.0000 | 25.0000 |
| Dimethicon (10 Cst) | — | 5.0000 |
| Cyclopentasiloxan | — | 1.0000 |
| Petrolatum | 5.0000 | 5.0000 |
| Ozokerit | 1.0000 | — |
| Stearylalcohol | 12.0000 | — |
| 2-Butyloctanic acid | 0.5000 | 0.5000 |
| Wax | — | 1.2500 |
| PPG-14 Butylether | 9.0000 | — |
| hydrogenated rapeseed oil | — | 5.0000 |
| Silicium dioxide | — | 1.0000 |
| Farnesol | 0.2500 | 0.2500 |
| Paraffin oil | 0.5000 | — |
| Castor wax | 3.5000 | — |
| Tallow | 4.0000 | — |
| Behenylalcohol | 0.2000 | — |
| d-Panthenyltriacetate | 1.0000 | — |
| Perfume composition A | 1.5000 | 1.1500 |
| Sum | 100.0000 | 100.0000 |

Example 19

Aerosol Spray

| material | A wt.-% |
|---|---|
| ethanol | 96.2000 |
| octyldodecanol | 0.5000 |
| 1,2-pentanediol | 1.0000 |
| 1,2-hexanediol | 0.2500 |
| 1,2-octanediol | 0.2500 |
| Farnesol | 0.5000 |
| ethylhexylglycerin | 0.5000 |
| perfume composition A | 0.8000 |
| Sum | 100.0000 |

Example 20

Sun Protection Spray

| Material | INCI | wt.-% |
|---|---|---|
| Phase A | | |
| Water, demineralized | Water (Aqua) | 68.9000 |
| Glycerin | Glycerin | 4.0000 |
| 1,3-Butylene glycol | Butylene Glycol | 5.0000 |
| D-Panthenol | Panthenol | 0.5000 |
| Lara Care A-200 | Galactoarabinan | 0.2500 |
| Phase B | | |
| Baysiloneöl M 10 | Dimethicone | 1.0000 |
| Edeta BD | Disodium EDTA | 0.1000 |
| Copherol 1250 | Tocopheryl Acetate | 0.5000 |
| Cetiol OE | Dicaprylyl Ether | 3.0000 |
| Neo Heliopan ® HMS | Homosalate | 5.0000 |
| Neo Heliopan ® AV | Ethylhexyl Methoxycinnamate | 6.0000 |
| Neo Heliopan ® 357 | Butyl Methoxydibenzoylmethane | 1.0000 |
| Corapan TQ | Diethylhexylnaphthalate | 2.0000 |
| Alpha Bisabolol | Bisabolol | 0.1000 |
| Pemulen TR-2 | Acrylates/C10-30 Alkyl Acrylate Crosspolymer | 0.2500 |
| Phase C | | |
| Phenoxyethanol | Phenoxyethanol | 0.7000 |
| Solbrol M | Methylparaben | 0.2000 |
| Solbrol P | Propylparaben | 0.1000 |
| Phase D | | |
| NaOH, 10% ig | Sodium Hydroxide | 0.6000 |
| Phase E | | 0.5000 |
| Perfume composition A | Perfume | 0.3000 |
| Sum | | 100.0000 |

Solve Lara Care A-200 in the ingredients of phase A by stirring. Mix all ingredients of phase B except the Pemulen and slightly heat until everything is solved. Add the Pemulen and homogenise. Then mix phase A and phase B and homogenise for 1 minute. Add phase C, D and E and homogenise with Ultra turrax for 1-2 minutes.

Example 21

Sun Protection Milk

| Material | INCI | wt.-% |
|---|---|---|
| Phase A | | |
| Dehymuls PGPH | Polyglyceryl-2 Dipolyhydroxystearate | 3.0000 |
| Beeswax 8100 | Beeswax | 1.0000 |
| Monomuls 90-0-18 | Glyceryl Oleate | 1.0000 |
| Zinc stearate | Zinc stearate | 1.0000 |
| Cetiol SN | Cetearyl Isononanoate | 5.0000 |
| Cetiol OE | Dicaprylyl Ether | 5.0000 |
| Tegosoft TN | C12-15 Alkyl Benzoate | 4.0000 |
| Vitamin E | Tocopherol | 0.5000 |
| Solbrol P | Propylparaben | 0.1000 |
| Neo Heliopan ® OS | Ethylhexyl Salicylate | 5.0000 |
| Neo Heliopan ® AV | Ethylhexyl Methoxycinnamate | 7.5000 |
| Uvinulâ T150 | Ethylhexyl Triazone | 1.5000 |
| Phase B | | |
| Water | Water | 43.5500 |
| Trilon BD | Disodium EDTA | 0.1000 |
| Glycerin | Glycerin | 5.0000 |
| Solbrol M | Methylparaben | 0.2000 |
| Phenoxyethanol | Phenoxyethanol | 0.7000 |
| Neo Heliopan ® AP 10% ige solution, neutralised with NaOH | Disodium Phenyl Dibenzimidazole Tetrasulfonate | 15.0000 |
| Phase C | | 0.5000 |
| Alpha Bisabolol | Bisabolol | 0.1000 |
| Perfume composition A | Perfume | 0.2500 |
| Sum | | 100.0000 |

The invention claimed is:

1. A product comprising:

(i) a container comprising at least one of polyethylene (PE), polypropylene (PP), and polyethylene terephthalate (PET); and (ii) a composition contained in the container, the composition comprising at least one compound from group (A) and/or group (B); at least one compound from group (C); at least one compound from group (D); and optionally, at least one compound from group (E), wherein groups (A), (B), (C), (D), and (E) are defined below:

(A) one or more compound(s) chosen from:

hydrocarbon terpenes with an oxygen percentage of 0, with respect to the molar mass of the compound, methyl anthranilate derivates of formula (I)

(I)

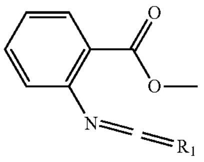

with $R_1$=H, methyl, benzylidene, (2,4-dimethylcyclohex-3-en-1-yl)methylene, 3-(4-tert-butylphenyl)-2-methyl-propylidene, 2,4-dimethylcyclohex-3-en-1-ylidene, [3-(1,3-benzodioxol-5-yl)-2-methyl-propylidene] or (7-hydroxy-3,7-dimethyl-octylidene), and with "N═R₁"="N═$R_1$" or "NH—$R_1$"; and phenolic derivatives of formula (II)

(II)

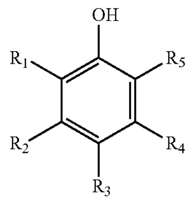

with $R_1$=H, methoxy, ethoxy, or tert-butyl, $R_2$/$R_4$=H, $R_3$=methyl, formyl, allyl, prop-1-enyl, hydroxy, or 3-oxobutyl, $R_5$=H, or tert-butyl: (B) I one or more compound(s) chosen from:

cyclic monoterpenes, chosen from bicyclic epoxy monoterpenes, monocyclic and bicyclic monoterpene alcohols and monoterpene ketones, and having formula (III): $C_{10}H_xO$ (III), with X=14-18, and having a molar mass of 150-154 g/mol, methoxybenzene derivatives of formula (IV)

(IV)

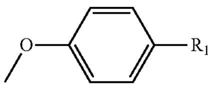

with $R_1$=methyl, prop-1-enyl, allyl, 3-oxobutyl, acetoxymethyl, 2-methyl-3-oxo-butyl, or 3-(2-ethylhexoxy)-3-oxo-prop-1-enyl, 2-hydroxybenzoic acid derivatives of formula (V)

(V)

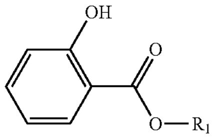

with $R_1$=methyl, ethyl, amyl, isoamyl, hexyl, 2-ethyl hexyl, cyclohexyl, hex-3-enyl, 2-phenylethyl, or benzyl;

benzoate derivatives of formula (VI)

(VI)

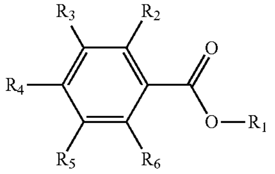

with $R_1$=methyl, ethyl, benzyl, or hexyl, $R_2$=H, hydroxy, or ethoxycarbonyl, $R_3$=H, or methyl, $R_4$=H, or hydroxy, $R_5$=H, $R_6$=H, or methyl, oxomethylbenzene derivatives of formula (VII)

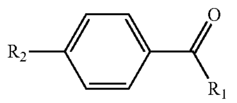

(VII)

with $R_1$=H, methyl, or phenyl, $R_2$=H, methyl, isopropyl, or methoxy, 3-oxopropylbenzene derivatives of formula (VIII)

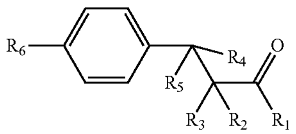

(VIII)

with $R_1$=H, or methyl, $R_2$=H, or methyl, $R_3$=H, or methyl, $R_4$=H, or methyl, $R_5$=H, or methyl, $R_6$=H, ethyl, or isopropyl, ligustral (mixture of (1R,2S)-2,4-dimethylcyclohex-3-ene-1-carbaldehyde and (18,2S)-2,4-dimethylcyclohex-3-ene-1-carbaldehyde), vertocitral (mixture of (1R,2S)-2,4-dimethylcyclohex-3-ene-1-carbaldehyde and (1S,2S)-2,4-dimethylcyclohex-3-ene-1-carbaldehyde), lyral (mixture of 4-(4-hydroxy-4-methyl-pentyl)cyclohex-3-ene-1-carbaldehyde and 3-(4-hydroxy-4-methyl-pentyl) cyclohex-3-ene-1-carbaldehyde), vertomugal (mixture of 4-(4-methylpent-3-enyl)cyclohex-3-ene-1-carbaldehyde and 3-(4-methylpent-3-enyl) cyclohex-3-ene-1-carbaldehyde), vernaldehyde (mixture of 3-isohexyl-1-methyl-cyclohex-3-ene-1-carbaldehyde and 4-isohexyl-1-methyl-cyclonex-3-ene-1-carbaldehyde), precyclemone B (mixture of 1-methyl-3-(4-methylpent-3-enyl)cyclohex-3-ene-1-carbaldehyde and 1-methyl-4-(4-methylpent-3-enyl)cyclohex-3-ene-1-carbaldehyde), styrene derivatives of formula (X)

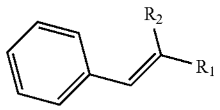

(X)

with $R_1$=H, methyl, or hydroxymethyl, $R_2$=H, formyl, methoxycarbonyl, or benzyloxycarbonyl, acetals with a molar mass of >225 g/mol and calculated water solubility of <0.6 mg/L, and cyclic ethers with a calculated water solubility of <2.5 mg/L;

(C) one or more compounds chosen from:

terpene derivatives chosen from: cyclic diterpene ketones selected from methyl ionone alpha, methyl ionone beta, methyl ionone gamma, methyl ionone beta, dihydroionone beta, isoradeine, allylionone, damascenone alpha, damascenone beta, damascenone gamma, damascenone delta, damascone beta, damascone delta, acyclic monoterpene esters, cyclic monoterpene esters, sesquiterpene esters and alcohols, acyclic monoterpene aldehydes selected from 2,6,10-trimethylundec-9-enal (Farenal®), (5E)-2,6,10-trimethylundeca-5,9-dienal (profarenal®), hydroxyl citronellal, citral, *eucalyptus* oil *citriodora*, lemongrass oil cochin, and acyclic monoterpene alcohols selected from linalool, terpineol, citronellol, nerol, nerolidol, farnesol, hydroxyl citronellol, isoamyl alcohol, osyrol (7-methoxy-3,7-dimethyl-octan-2-ol), tetrahydro geraniol, tetrahydro muguol (mixture of tetrahydro myrcenol and tetrahydro linalool), tetrahydro myrcenol, ethyl linalool, isobornyl cyclohexanol, 1-[(1S,6S)-2,2,6-trimethylcyclohexyl]pentan-3-ol (madranol®), 1-(2,2,6-trimethylcyclohexyl)hexan-3-ol (timberol®), thymol, mayol ((4-isopropylcyclohexyl)methanol), dihydro terpineol, menthol, menthol rac., pine oil, coriander oil, palmarosa oil:

acetals with a molar mass of <225 g/mol and calculated water solubility of >0.6 mg/L, acids, alcohols chosen from phenylethyl alcohol, ambrinol ((2S 4aS)-2,5,5-trimethyl-1,3,4,4a,6,7-hexahydronaphthalen-2-ol), amber core (mixture of 1-[(1R,2R)-2-tert-butylcyclohexoxy]butan-2-ol, 1-[(1S,2R)-2-tert-butylcyclohexoxy]butan-2-ol and 2-(2-tert-butylcyclohexoxy)butan-1-ol), 2-methyl-4-(2,2,3-trimethylcyclopent-3-en-1-yl) butan-1-ol (Branhmanol®), kohinool, mugetanol (mixture of cis-1-(4-isopropylcyclohexyl)ethanol and trans-1-(4-isopropylcyclohexyl)ethanol), polysantol ((E)-3,3-dimethyl-5-(2,2,3-trimethylcyclopent-3-en-1-yl)pent-4-en-2-ol), alcohol C12, jasmol, sandalore (mixture of 3-methyl-5-(2,2,3-trimethylcyclopent-3-en-1-yl)pentan-2-ol and 6-(2,2,3-trimethylcyclopent-3-en-1-yl)nexan-3-ol), anisyl alcohol, hexanol, octanol, decanol, benzyl alcohol, butyl cyclohexanol para-tert, decenol-9, ebanol (mixture of (E,2S,3R)-3-methyl-5-(2,2,3-trimethylcyclopent-3-en-1-yl)pent-4-en-2-ol and (E,2R,3R)-3-methyl-5-(2,2,3-trimethylcyclopent-3-en-1-yl)pent-4-en-2-ol), florosa, furaneol, cis-3-hexenol, 2,2-dimethyl-3-(m-tolyl)propan-1-ol (Majantol®), methyl methoxy butanol-3,3, muguetalcohol (2,2-dimethyl-3-phenyl-propan-1-ol), phenoxanol (3-methyl-5-phenyl-pentan-1-ol), phenoxyethyl alcohol, phenyl dimethyl carbinol, phenylethyl methylethyl carbinol, phenylpropyl alcohol, (2-methyl-5-phenyl-pentan-1-ol) (Rosaphen®), sandal mysore core ((E)-2-methyl-4-(2,2,3-trimethylcyclopent-3-en-1-yl)but-2-en-1-ol), (E)-2-ethyl-4-(2 2,3-trimethylcyclopent-3-en-1-yl)but-2-en-1-ol (San-Dranol®), styralyl alcohol, 4-isopentylcyclohexanol (Symrose®), dihydro eugenol, propenyl quaethol, cresol para, ambrinolepoxide ((1aR,4aS,7S,8aS)-4,4,7-trimethyl-2,3,4a,5,6,8-hexahydro-1aH-naphtho[1,8a-bloxiren-7-ol), one or more of ethers and cyclic ethers with a calculated water solubility of >2.5 mg/L, aldehydes selected from aldehyde C12 MNA, neocyclo citral, aldehyde C11 MOA, hexyl cinnamic aldehyde alpha, cyclomyral, amyl cinnamic aldehyde, 2,6-dimethylhept-5-enal (Melonal®), nonanal, isononyl aldehyde S, octanal, aldehyde C11 iso, intreleven aldehyde (mixture of undec-10-enal, 9-undecenal and 8-undecenal), lilial(3-(4-tert-butylohenyl)-2-methyl-propanal), hexanal, heptanal, silvial (3-(4-isobutylphenyl)-2-methyl-propanal), 2-trans-hexenal, scentenal (octahydro-5-methoxy-4,7-methano-1H-indene-2-carboxaldehyde), phenylacetaldehyde, mandarin aldehyde (2E-dodecenal), esters chosen from pyroprunat ((2-cyclopentylcyclopentyl) (E)-but-2-enoate), hercolyn D-E (mixture of methyl 7-isopropyl-1,4a-dimethyl-2,3,4,5,6,7,8,9,10,10a-decahydrophenanthrene-1-carboxylate and methyl 7-isopropyl-1,4a-dimethyl-2,3,4,9,10,10a-hexahydrophenanthrene-1-carboxylate), fruitate, cyclabute (3a,4,5,6,7,7a-hexahydro-4,7-methano-1H-inden-5-yl 2-methyl propanoate), poivrol (mixture of methyl (1S,4R,5R)-4-isopropyl-1-methyl-bicyclo[2.2.2]oct-2-ene-5-carboxylate, methyl (1S,4R,5S)-4-isopropyl-1-methyl-bicyclo[2.2.2]oct-2-ene-5-carboxylate, methyl (1R,2S,4R)-4-isopropyl-1-methyl-bicyclo[2.2.2]oct-5-ene-2-carboxylate and methyl (1R,2R,4R)-4-isopropyl-1-methyl-bicyclo[2.2.2]oct-5-ene-2-carboxylate), guaiyl acetate, herbyl propionate (hexahydro-4,7-methanoinden-5(or 6)-yl propionate), vetiveryl acetate, nopyl acetate, hydroherbaflorat, herbaflorat (hexahydro-4,7-methanoinden-(5 and 6)-yl acetate), ethyl cinnamate, phenylethyl cinnamate, isoeugenyl methyl ether, isoeugenyl acetate, eugenyl acetate, ethyl benzoate, isobutyl salicylate, prenyl salicylate, dimethyl benzyl carbonyl butyrate, phenylethyl isovalerate, benzyl butyrate, benzyl isobutyrate, dimethyl benzyl carbonyl acetate, phenylethyl isobutyrate, benzyl propionate, phenylethyl acetate, (1,3-dimethyl-3-phenyl-butyl) acetate (Vetikolaceate®), benzyl acetate, ethyl phenyl acetate, methyl phenyl acetate, styralyl acetate, phenylethyl phenylacetate, benzyl formiate, 2-phenoxyethyl 2-methylpropanoate (Phenirate®), benzyl phenylacetate, aldehyde C16 so-called, allyl phenoxy acetate, cresyl phenyl acetate para, rosacetate, hexyl caproate, ethyl caprinate, decyl acetate, ethyl caprylate, hexyl butyrate, hexyl isobutyrate, ethyl heptoate, isoamyl butyrate, butyl butyrate, allyl heptoate, ethyl caproate, manzanate, neononyl acetate, ethyl methyl butyrate-2, frutinat, isopentyrate, ethyl butyrate, ethyl isovalerate, amyl acetate, hexyl acetate, ethyl isobutyrate, butyl acetate, isobutyl acetate, ethyl propionate, cis-3-hexenylacetate, [(Z)-hex-3-enyl]methyl carbonate (Leafovert®), prenyl acetate, methyl octin carbonate, allyl amyl glycolate, ethyl acetate, butyl butyryl lactate, diethylmalonate, ethyl acetoacetate, (3-hydroxy-2,2,4-trimethyl-pentyl) 2-methylpropanoate (Symfresh® NX), allyl cyclohexyl propionate, givescone (mixture of ethyl 2,3,6,6-tetramethylcyclonex-2-ene-1-carboxylate and ethyl 2-ethyl-6,6-dimethyl-cyclohex-2-ene-1-carboxylate), mintonat (mixture of [(1S,5S)-3,3,5-trimethylcyclohexyl]acetate and [(1R,5S)-3,3,5-trimethylcyclohexyl]acetate), oryclon ((4-tert-butylcyclohexyl) acetate), aphermate (1-(3,3-dimethylcyclohexyl)ethyl formate), cyclohexyl ethyl acetate, datilat (1-cyclohexylethyl (E)-but-2-enoate), helvetolide (2-[1-(3,3-dimethylcyclohexyl)ethoxy]-2-methyl-propyl]propanoate), myraldyl acetate (mixture of [38-(4-methylpent-3-enyl)cyclohex-3-en-1-yl]methyl acetate and [4-(4-methylpent-3-enyl)cyclohex-3-en-1-yl]methyl acetate), cyclohexyl acetate, allyl 2-(cyclohexoxy) acetate (Cyclogalbanate®), jasmopyrane ((3-pentyltetrahydropyran-4-yl) acetate), jessemal ((3-butyl tetrahydro-5-methyl-2H-pyran-4-yl) acetate, ethylene brassylate (1,4-dioxacyclohneptadecane-5,17-dione), ethylene dodecanedioate arova N, ethyl 2-(2,4-dimethyl-1,3-dioxolan-2-yl)acetate (Fragolane®), hedione (mixture of methyl 2-[(1S,2S)-3-oxo-2-pentyl-cyclopentyllacetate and methyl 2-[(1S,2R)-3-oxo-2-pentyl-cyclopentyllacetate, jasmaprunat (ethyl 2-(2-methyl-1,3-dioxolan-2-yl)acetate), jasmopol AC 1300 (methyl 2-hexyl-3-oxo-cyclopentanecarboxylate), maltol isobutyrate, triethyl citrate, ethers and cyclic ethers with a calculated water solubility of >2.5 mg/L selected from the group consisting of anther, rose oxide HC (mixture of (2R,4S)-4-methyl-2-(2-methylprop-1-enyl)tetrahydropyran and (2S,4S)-4-methyl-2-(2-methylprop-1-enyl)tetrahydropyran), rose oxide L (mixture of (2R,4S)-4-methyl-2-(2-methylprop-1-enyl)tetrahydropyran and (2S,4S)-4-methyl-2-(2-methylprop-1-enyl)tetrahydropyran), rose oxide inactive (mixture of (2R,4S)-4-methyl-2-(2-methylprop-1-enyl)tetrahydropyran and (2S,4S)-4-methyl-2-(2-methylprop-1-enyl)tetrahydropyran), diphenyl oxide, phenylethyl methyl ether, dibenzyl ether, kephalis (4-(1-ethoxyvinyl)-3,3,5,5-tetramethyl-cyclohexanone), linalool oxide, dowanol DPM (3-(3-methoxypropoxy)propan-1-ol), heterocyclic compounds, ketones selected from cyclohexadecanone (Isomuscone®), vertofix, veloutone, muscenone, 4-[(3,3-dimethylnorbornan-2-yl)methyl]-2-methyl-cyclohexanone (Aldron®), isolongifolanon (octahydrotetramethyl methanoazulenone), (8E)-cyclohexadec-8-en-1-one (Globanone®), 2,4,4,7-tetramethyloct-6-en-3-one (Claritone®), iso e super (mixture of 1-[2R,3R)-2,3,8,8-tetramethyl-1,3,4,5,6,7-hexahydronaphthalen-2-yllethanone, 1-(2,3,8,8-tetramethyl-1,3,5,6,7,8a-hexahydronaphthalen-2-yllethanone and 1-[(2S 3S)-2,3,8,8-tetramethyl-1,3,5,6,7 8a-hexahydronaphthalen-2-yllethanone), (8E)-cyclonexadec-8-en-1-one (Aurelione®), projasmone P (2-heptylcyclopentanone), frescomenthe (2-sec-butylcyclohexanone), dynascone (mixture of 1-(5,5-dimethylcyclohexen-1-yl)pent-4-en-1-one, 1-(3,3-dimethylcyclohexen-1-yl)pent-4-en-1-one and (E)-1-(2,6,6-trimethylcyclohex-2-en-1-yl) but-2-en-1-one), galbascone (1-(5,5-dimethylcyclohexen-1-yl)pent-4-en-1-one), undecanone-2, kKoavone (mixture of (E)-3,4,5,6,6-pentamethylhept-4-en-2-one, 3,5,6,6-tetramethyl-4-methylene-heptan-2-one and (E)-3,4,5,6,6-pentamethylhept-3-en-2-one), tonalide (1-(1,1,2,4,4,7-hexamethyltetralin-6-yl)ethanone), nerolione (1-(3-methylbenzofuran-2-yl)ethanone), octanone-2, cashmeran (1,1,2,3,3-pentamethyl-2,5,6,7-tetrahydroinden-4-one), orivone (4-(1,1-dimethylpropyl)cyclohexanone), azarbre (mixture of 3,5-diethyl-2,5-dimethyl-cyclohex-2-en-1-one and 3,5-diethyl-5,6-dimethyl-cyclohex-2-en-1-one), methyl heptenone-6,5,2, dihydro jasmine (3-methyl-2-pentyl-cyclopent-2-en-1-one), jasmine cis (3-methyl-2-[(Z)-pent-2-enyl]cyclopent-2-en-1-one), acetanisole, calone 1951 (7-methyl-1,5-benzodioxepin-3-one), acetyl methyl carbinol, crysolide (1-(6-tert-butyl-1,1-dimethyl-indan-4-yl)ethanone), ethyl maltol, maltol, methyl cyclopentenolone-3,2,2, lactones, and nitriles;

(D) water and/or one or more solvent(s) chosen from ethanol, dipropylene glycol (DPG), diethylphtalate (DEP), propylene glycol (PG), isopropylmyristate (IPM), isopropylpalmitate (IPP) triethylcitrate (TEC), 2-propanol, triacetin (TRI), 1,2-propanediol, 1,3-propanediol, propanetriol, 1,2-pentanediol (Hydrolite®-5), 1,2-hexanediol (Hydrolite®-6), 1,2-octanediol (Hydrolite®-8), 1,2-decanediol (SymClariol®), dodecanol, 4-hydroxy-acetophenone (SymSave® H), glycerin, butylenes glycol, pentylene glycol, hexylene glycol, decylene glycol, propylene carbonate, butylenes carbonate, glycerin carbonate, 2-benzylheptanol, laurylalcohol, trimethylhydroxypentyl-isobutyrat, glycerylcaprylate, ethylhexylglycerin, benzylbenzoate (BB), Isoparaffine, glycol ether, and dowanol: and (E) optionally, one or more surface active compound(s) chosen from alkyl carboxylate, alkyl sulfonate, alkyl sulphate, alcohol polyglycol ether sulfate, quaternary ammonium cations, quaternary ammonium ester, alcohol polyglycol ether, N-(Acylaminoalkyl)-betaine, polyethylene glycol alkyl ether, alkyl benzene sulfonate, TEA-esterquat:

wherein the total amount of compound(s) of group (A), if present, is 0.5 wt. % or less; and the total amount of compound(s) of group (B), if present, is less than 10 wt. %; and wherein the total amount of compound(s) of group (C) is 20 wt. % or less, in each case based on the total amount of the composition; and the composition contained in the container does not cause a visual and/or weight change to packaging consisting of PE, PP, or PET after 4 weeks at 40° C.

2. The product of claim 1, wherein the acetals with a molar mass of <225 g/mol and calculated water solubility of >0.6 mg/L are selected from 2-isobutyl-4-vinyl-1,3-dioxolane, 6,6-dimethoxy-2,5,5-trimethyl-hex-2-ene (Amarocit®), hyacinth body, floropal, magnolan, (2R,4S)-2-methyl-4-phenyl-1,3-dioxolane (Jacinthaflor®), phenylacetaldehyde dimethyl acetal, 4,4a,5,9b-tetrahydroindeno[1,2-d][1,3]dioxine (Indoflor®), citral diethyl acetal, hydroxyl citronellal dimetacetal, phenylacetaldehyde glyceryl acet, heliotropin, and helional.

3. The product of claim 1, wherein the hydrocarbon terpenes with an oxygen percentage of 0, with respect to the molar mass of the compound, are selected from cedrene ((1S,2R,5S)-2,6,6,8-tetramethyltricyclo[5.3.1.01.5]undec-8-ene), caryophyllene, ginger oil chinese, gurjun balsam oil, gurjun balsam siam, limonene (4-isopropenyl-1-methyl-cyclohexene), terpinene, phellandrene, pepper black oil, pine needle oil chinese, grapefruit oil, tangerine cravo oil brazil, mandarin oil ital., orange oil brazil, lime oil terpenes, lemon oil terpenes, elemi oil, cymene para, citrylal, pinene alpha, carene delta-3, camphene, pinene beta, dipentene, turpentine oil portug., and myrcene.

4. The product of claim 1, wherein the methyl anthranilate derivates of formula (I) are selected from methyl anthranilate, dimethylanthranilate, vertosine (methyl 2-[(E)-(2,4-dimethylcyclohex-3-en-1-yl)methyleneamino]benzoate), verdantiol (methyl 2-[(E)-[3-(4-tert-butylphenyl)-2-methyl-propylidene]amino]benzoate), aurantiol (methyl 2-[(E)-(7-hydroxy-3,7-dimethyl-octylidene)amino]benzoate), amandolene (methyl N-benzylideneanthranilate), meaverte (methyl 2-[(2,4-dimethylcyclohex-3-en-1-ylidene)methylamino]benzoate), and heliosine (methyl 2-[(E)[3-(1,3-benzodioxol-5-yl)-2-methyl-propylidene]amino]benzoate).

5. The product of claim 1, wherein the phenolic derivatives of formula (II) are selected from ethyl vanillin, eugenol, vanillin, isoeugenol, BHT ionol, 4-(4-hydroxyphenyl) butan-2-one (Frambinon®), essential oils selected from the group consisting of clove leaves oil, cinnamon leaf oil, and cinnamon leaf oil discolored.

6. The product of claim 1, wherein the cyclic monoterpenes of formula (III) are selected from fenchol, isoborneol, borneol, eucalyptol, 1,4-cineol, *eucalyptus* oil, camphor, menthone, isomenthone, carvone, and spearmint oil 65% americ. native.

7. The product of claim 1, wherein the methoxybenzene derivatives of formula (IV) are selected from cresyl methyl ether para, estragole, 4-(4-methoxyphenyl)butan-2-one (Frambinon® methyl ether), anisyl acetate, canthoxal (3-(4-methoxyphenyl)-2-methyl-propanal), and 2-ethylhexyl (E)-3-(4-methoxyphenyl)prop-2-enoate (Neo Heliopan® AV).

8. The product of claim 1, wherein the 2-hydroxybenzoic acid derivatives of formula (V) are selected from methyl salicylate, ethyl salicylate, amyl salicylate, isoamyl salicylate, hexyl salicylate, 2-ethyl hexyl salicylate, and 3-hexenyl salicylate.

9. The product of claim 1, wherein the benzoate derivatives of formula (VI) are selected from methyl benzoate, evernyl (methyl 2,4-dihydroxy-3,6-dimethyl-benzoate), benzyl benzoate, hexyl benzoate, diethylphtalate.

10. The product of claim 1, wherein the oxomethylbenzene derivatives of formula (VII) are selected from benzaldehyde, tolylaldehyde para, cuminic aldehyde, acetophenone, methyl acetophenone, benzophenone, and anisic aldehyde.

11. The product of claim 1, wherein the 3-oxopropylbenzene derivatives of formula (VIII) are selected from florazon (mixture of 3-(4-ethylphenyl)-2,2-dimethyl-propanal and 3-(2-ethylphenyl)-2,2-dimethyl-propanal), floralozone (mixture of 3-(4-ethylphenyl)-2,2-dimethyl-propanal and 3-(2-ethylphenyl)-2,2-dimethyl-propanal), 4-methyl-4-phenyl-pentan-2-one (Vetikon®) and benzylacetone, cyclamen aldehyde (3-(4-isopropylphenyl)-2-methyl-propanal), and florhydral (3-(3-isopropylphenyl)butanal).

12. The product of claim 1, wherein the styrene derivatives of formula (X) are selected from the group consisting of styrene, methyl cinnamic aldehyde, methyl cinnamate, benzyl cinnamate, and cinnamic alcohol.

13. The product of claim 1, wherein the one or more solvent(s) are selected from the group consisting of ethanol, DPG, PG, IPM, TEC, 1,2-propanediol, 1,3-propanediol, propanetriol, 1,2-pentanediol (Hydrolite®-5), 1,2-hexanediol (Hydrolite®-6), 1,2-octanediol (Hydrolite®-8), 1,2-decanediol (SymClariol®), dodecanol, 4-hydroxy-acetophenone (SymSave® H), glycerine, and isopar-L.

14. The product of claim 1, wherein the one or more surface active compound(s) are selected from the group consisting of lauryl ether sulfate, betaine, lauryl alkyl sulfate, PEG hydrogenated castor oil, laureth-5, laureth-6, laureth-7, Dialkylesterammoniumethosulfate, sodium stearate, sodium palmitate, polyethylene glycol, zinc stearate, sodium caprylate, lauric acid, Isopar-L, sodium dodecyl benzene sulfonate, and Dihydrogenated Tallowethyl Hydroxyethylmonium Methosulfate.

15. The product of claim 1, wherein the container comprises PE and/or PP.

16. The product of claim 1, wherein the container is in the form of a wrapping, an encasement, a packaging, a shell, a coating, or an envelope.

17. The product of claim 1, wherein the total amount of compound(s) of group (A), if present, is in the range of from 0.05 wt. % to 0.5 wt. % and the total amount of compound(s) of group (B), if present, is in the range of from 0.01 wt. % to less than 10 wt. %, in each case based on the total amount of the composition.

18. The product of claim 1, wherein the total amount of compound(s) of group (A), if present, is in the range of from 0.05 wt. % to 0.5 wt. % and the total amount of compound(s) of group (B), if present, is in the range of from 0.01 wt. % to 1.25 wt. %, in each case based on the total amount of the composition.

19. The product of claim 1, wherein the total amount of water according to component (D), if present, is in the range of from 35 wt. % to 99 wt. %, based on the total amount of the composition.

20. A method for producing a product according to claim 1 comprising:

(I) providing a container (i) comprising at least one of polyethylene (PE), polypropylene (PP), and polyethylene terephthalate (PET);

(II) providing a composition (ii) of claim 1;

(III) filling the container (i) with the composition (ii);

(IV) optionally, adding one or more further substances into the container (i), and (V) optionally, closing and/or sealing the container (i).

* * * * *